(12) United States Patent
Schechter et al.

(10) Patent No.: US 7,776,036 B2
(45) Date of Patent: *Aug. 17, 2010

(54) BIPOLAR CONCENTRIC ELECTRODE ASSEMBLY FOR SOFT TISSUE FUSION

(75) Inventors: David A. Schechter, Longmont, CO (US); Philip Tetzlaff, Lafayette, CO (US); Jeffrey M. Roy, Boulder, CO (US)

(73) Assignee: Covidien AG, Neuhausen am Rheinfall (CH)

( * ) Notice: Subject to any disclaimer, the term of this patent is extended or adjusted under 35 U.S.C. 154(b) by 952 days.

This patent is subject to a terminal disclaimer.

(21) Appl. No.: 10/548,683

(22) PCT Filed: Mar. 13, 2003

(86) PCT No.: PCT/US03/08146

§ 371 (c)(1),
(2), (4) Date: Nov. 8, 2006

(87) PCT Pub. No.: WO2004/082495

PCT Pub. Date: Sep. 30, 2004

(65) Prior Publication Data

US 2007/0156139 A1 Jul. 5, 2007

(51) Int. Cl.
*A61B 18/18* (2006.01)
(52) U.S. Cl. .......................................... 606/51; 606/50
(58) Field of Classification Search ............. 606/48–52, 606/205–207
See application file for complete search history.

(56) References Cited

U.S. PATENT DOCUMENTS

| | | | |
|---|---|---|---|
| 371,664 A | 10/1887 | Brannan et al. | |
| 702,472 A | 6/1902 | Pignolet | |
| 728,883 A | 5/1903 | Downes | |
| 1,586,645 A | 6/1926 | Bierman | |
| 1,813,902 A | 7/1931 | Bovie | |
| 1,822,330 A | 9/1931 | Ainslie | |
| 1,852,542 A | 4/1932 | Sovatkin | |
| 2,002,594 A | 5/1935 | Wappler et al. | |

(Continued)

FOREIGN PATENT DOCUMENTS

CA  2104423  2/1994

(Continued)

OTHER PUBLICATIONS

Int'l Search Report EP 06 020574.7 dated Sep. 21, 2007.

(Continued)

*Primary Examiner*—Michael Peffley

(57) ABSTRACT

A bipolar electrosurgical forceps for treating tissue includes a pair of opposing first and second jaw members each having a tissue engaging surface disposed thereon. Each of the jaw members is movable relative to one another from a first position to approximate tissue to a second position for engaging tissue therebetween. The first jaw member includes a plurality of ring electrodes disposed thereon having a first electrical potential and the second jaw member includes a corresponding plurality of post electrodes disposed thereon having a second electrical potential. Each of the plurality of post electrodes is inwardly disposed of a respective ring electrode to form an electrode micro-sealing pad wherein upon activation of the forceps tissue grasped between each electrode micro-sealing pad is sealed while tissue adjacent to each electrode micro-sealing pads remains viable.

24 Claims, 10 Drawing Sheets

U.S. PATENT DOCUMENTS

| | | |
|---|---|---|
| 2,011,169 A | 8/1935 | Wappler |
| 2,031,682 A | 2/1936 | Wappler et al. |
| 2,054,149 A | 9/1936 | Wappler |
| 2,176,479 A | 10/1939 | Willis |
| 2,305,156 A | 4/1941 | Grubel |
| 2,279,753 A | 4/1942 | Knopp |
| 2,327,353 A | 8/1943 | Karle |
| 2,632,661 A | 8/1948 | Cristofv |
| 2,668,538 A | 2/1954 | Baker |
| 2,796,065 A | 6/1957 | Kapp |
| 3,073,311 A | 1/1963 | Tibbs et al. |
| 3,372,288 A | 3/1968 | Wigington |
| 3,459,187 A | 8/1969 | Pallotta |
| 3,643,663 A | 2/1972 | Sutter |
| 3,648,001 A | 3/1972 | Anderson et al. |
| 3,651,811 A | 3/1972 | Hildebrandt et al. |
| 3,678,229 A | 7/1972 | Osika |
| 3,720,896 A | 3/1973 | Beierlein |
| 3,763,726 A | 10/1973 | Hildebrand |
| 3,779,918 A | 12/1973 | Ikeda et al. |
| 3,801,766 A | 4/1974 | Morrison, Jr. |
| 3,862,630 A | 1/1975 | Balamuth |
| 3,863,339 A | 2/1975 | Reaney et al. |
| 3,866,610 A | 2/1975 | Kletschka |
| 3,911,766 A | 10/1975 | Fridolph et al. |
| 3,920,021 A | 11/1975 | Hiltebrandt |
| 3,921,641 A | 11/1975 | Hulka |
| 3,938,527 A | 2/1976 | Rioux et al. |
| 3,952,749 A | 4/1976 | Fridolph et al. |
| 3,970,088 A | 7/1976 | Morrison |
| 3,987,795 A | 10/1976 | Morrison |
| 4,005,714 A | 2/1977 | Hiltebrandt |
| 4,016,881 A | 4/1977 | Rioux et al. |
| 4,041,952 A | 8/1977 | Morrison, Jr. et al. |
| 4,043,342 A | 8/1977 | Morrison, Jr. |
| 4,074,718 A | 2/1978 | Morrison, Jr. |
| 4,076,028 A | 2/1978 | Simmons |
| 4,080,820 A | 3/1978 | Allen |
| 4,088,134 A | 5/1978 | Mazzariello |
| 4,112,950 A | 9/1978 | Pike |
| 4,127,222 A | 11/1978 | Adams |
| 4,128,099 A | 12/1978 | Bauer |
| 4,165,746 A | 8/1979 | Burgin |
| 4,187,420 A | 2/1980 | Piber |
| 4,233,734 A | 11/1980 | Bies |
| 4,236,470 A | 12/1980 | Stenson |
| 4,300,564 A | 11/1981 | Furihata |
| 4,311,145 A | 1/1982 | Esty et al. |
| D263,020 S | 2/1982 | Rau, III |
| 4,370,980 A | 2/1983 | Lottick |
| 4,375,218 A | 3/1983 | DiGeronimo |
| 4,416,276 A | 11/1983 | Newton et al. |
| 4,418,692 A | 12/1983 | Guay |
| 4,443,935 A | 4/1984 | Zamba et al. |
| 4,452,246 A | 6/1984 | Bader et al. |
| 4,470,786 A | 9/1984 | Sano et al. |
| 4,492,231 A | 1/1985 | Auth |
| 4,493,320 A | 1/1985 | Treat |
| 4,503,855 A | 3/1985 | Maslanka |
| 4,506,669 A | 3/1985 | Blake, III |
| 4,509,518 A | 4/1985 | McGarry et al. |
| 4,552,143 A | 11/1985 | Lottick |
| 4,574,804 A | 3/1986 | Kurwa |
| 4,597,379 A | 7/1986 | Kihn et al. |
| 4,600,007 A | 7/1986 | Lahodny et al. |
| 4,624,254 A | 11/1986 | McGarry et al. |
| 4,655,215 A | 4/1987 | Pike |
| 4,655,216 A | 4/1987 | Tischer |
| 4,657,016 A | 4/1987 | Garito et al. |
| 4,662,372 A | 5/1987 | Sharkany et al. |
| 4,671,274 A | 6/1987 | Sorochenko |
| 4,685,459 A | 8/1987 | Xoch et al. |
| 4,733,662 A | 3/1988 | DeSatnick et al. |
| D295,893 S | 5/1988 | Sharkany et al. |
| D295,894 S | 5/1988 | Sharkany et al. |
| 4,754,892 A | 7/1988 | Retief |
| 4,763,669 A | 8/1988 | Jaeger |
| 4,827,929 A | 5/1989 | Hodge |
| 4,829,313 A | 5/1989 | Taggart |
| 4,846,171 A | 7/1989 | Kauphusman et al. |
| 4,887,612 A | 12/1989 | Esser et al. |
| 4,938,761 A | 7/1990 | Ensslin |
| 4,947,009 A | 8/1990 | Osika et al. |
| 4,985,030 A | 1/1991 | Melzer et al. |
| 5,007,908 A | 4/1991 | Rydell |
| 5,026,370 A | 6/1991 | Lottick |
| 5,026,371 A | 6/1991 | Rydell et al. |
| 5,035,695 A | 7/1991 | Weber, Jr. et al. |
| 5,037,433 A | 8/1991 | Wilk et al. |
| 5,042,707 A | 8/1991 | Taheri |
| 5,047,046 A | 9/1991 | Bodoia |
| 5,078,716 A | 1/1992 | Doll |
| 5,084,057 A | 1/1992 | Green et al. |
| 5,085,659 A | 2/1992 | Rydell |
| 5,099,840 A | 3/1992 | Goble et al. |
| 5,100,430 A | 3/1992 | Avellanet et al. |
| 5,108,392 A | 4/1992 | Spingler |
| 5,112,343 A | 5/1992 | Thornton |
| 5,116,332 A | 5/1992 | Lottick |
| 5,147,357 A | 9/1992 | Rose et al. |
| 5,151,102 A | 9/1992 | Xamiyama et al. |
| 5,151,978 A | 9/1992 | Bronikowski et al. |
| 5,176,695 A | 1/1993 | Dulebohn |
| 5,190,541 A | 3/1993 | Abele et al. |
| 5,196,009 A | 3/1993 | Kirwan, Jr. |
| 5,197,964 A | 3/1993 | Parins |
| 5,209,747 A | 5/1993 | Knoepfler |
| 5,211,655 A | 5/1993 | Hasson |
| 5,215,101 A | 6/1993 | Jacobs et al. |
| 5,217,457 A | 6/1993 | Delahuerga et al. |
| 5,217,458 A | 6/1993 | Parins |
| 5,217,460 A | 6/1993 | Knoepfler |
| 5,219,354 A | 6/1993 | Choudhury et al. |
| 5,244,462 A | 9/1993 | Delahuerga et al. |
| 5,250,047 A | 10/1993 | Rydell |
| 5,250,063 A | 10/1993 | Abidin et al. |
| 5,258,001 A | 11/1993 | Corman |
| 5,258,006 A | 11/1993 | Rydell et al. |
| 5,261,918 A | 11/1993 | Phillips et al. |
| 5,275,615 A | 1/1994 | Rose |
| 5,277,201 A | 1/1994 | Stern |
| 5,282,799 A | 2/1994 | Rydell |
| 5,282,800 A | 2/1994 | Foshee et al. |
| 5,282,826 A | 2/1994 | Quadri |
| 5,290,286 A | 3/1994 | Parins |
| 5,300,082 A | 4/1994 | Sharpe et al. |
| 5,304,203 A | 4/1994 | El-Mallawany et al. |
| 5,308,353 A | 5/1994 | Beurrier |
| 5,308,357 A | 5/1994 | Lichtman |
| 5,313,027 A | 5/1994 | Inoue et al. |
| 5,314,445 A | 5/1994 | Degwitz et al. |
| 5,318,589 A | 6/1994 | Lichtman |
| 5,324,289 A | 6/1994 | Eggers |
| D348,930 S | 7/1994 | Olson |
| 5,326,806 A | 7/1994 | Yokoshima et al. |
| 5,330,471 A | 7/1994 | Eggers |
| 5,330,502 A | 7/1994 | Hassler et al. |
| 5,334,183 A | 8/1994 | Wuchinich |
| 5,334,215 A | 8/1994 | Chen |
| 5,336,220 A | 8/1994 | Ryan et al. |
| 5,336,221 A | 8/1994 | Anderson |
| 5,342,359 A | 8/1994 | Rydell |
| 5,342,381 A | 8/1994 | Tidemand |
| 5,342,393 A | 8/1994 | Stack |

| Patent No. | Date | Name |
|---|---|---|
| 5,344,424 A | 9/1994 | Roberts et al. |
| 5,350,391 A | 9/1994 | Iacovelli |
| 5,352,222 A | 10/1994 | Rydell |
| 5,354,271 A | 10/1994 | Voda |
| 5,356,408 A | 10/1994 | Rydell |
| 5,366,477 A | 11/1994 | LeMarie, III et al. |
| 5,368,600 A | 11/1994 | Failla et al. |
| 5,374,277 A | 12/1994 | Hassler |
| 5,376,089 A | 12/1994 | Smith |
| 5,383,875 A | 1/1995 | Bays et al. |
| 5,383,897 A | 1/1995 | Wholey |
| 5,389,098 A | 2/1995 | Tsuruta et al. |
| 5,389,103 A | 2/1995 | Melzer et al. |
| 5,389,104 A | 2/1995 | Hahnen et al. |
| 5,391,166 A | 2/1995 | Eggers |
| 5,391,183 A | 2/1995 | Janzen et al. |
| 5,396,900 A | 3/1995 | Slater et al. |
| 5,403,312 A | 4/1995 | Yates et al. |
| 5,403,342 A | 4/1995 | Tovey et al. |
| 5,405,344 A | 4/1995 | Williamson et al. |
| 5,409,763 A | 4/1995 | Serizawa et al. |
| 5,411,519 A | 5/1995 | Tovey et al. |
| 5,411,520 A | 5/1995 | Nash et al. |
| 5,413,571 A | 5/1995 | Katsaros et al. |
| 5,415,656 A | 5/1995 | Tihon et al. |
| 5,415,657 A | 5/1995 | Taymor-Luria |
| 5,422,567 A | 6/1995 | Matsunaga |
| 5,423,810 A | 6/1995 | Goble et al. |
| 5,425,690 A | 6/1995 | Chang |
| 5,425,739 A | 6/1995 | Jessen |
| 5,429,616 A | 7/1995 | Schaffer |
| 5,431,672 A | 7/1995 | Cote et al. |
| 5,431,674 A | 7/1995 | Basile et al. |
| 5,437,292 A | 8/1995 | Kipshidze et al. |
| 5,438,302 A | 8/1995 | Goble |
| 5,439,478 A | 8/1995 | Palmer |
| 5,441,517 A | 8/1995 | Kensey et al. |
| 5,443,463 A | 8/1995 | Stern et al. |
| 5,443,464 A | 8/1995 | Russell et al. |
| 5,443,480 A | 8/1995 | Jacobs et al. |
| 5,445,638 A | 8/1995 | Rydell et al. |
| 5,445,658 A | 8/1995 | Durrfeld et al. |
| 5,449,480 A | 9/1995 | Kuriya et al. |
| 5,451,224 A | 9/1995 | Goble et al. |
| 5,454,823 A | 10/1995 | Richardson et al. |
| 5,454,827 A | 10/1995 | Aust et al. |
| 5,456,684 A | 10/1995 | Schmidt et al. |
| 5,458,598 A | 10/1995 | Feinberg et al. |
| 5,460,629 A | 10/1995 | Shlain et al. |
| 5,461,765 A | 10/1995 | Linden et al. |
| 5,462,546 A | 10/1995 | Rydell |
| 5,472,442 A | 12/1995 | Klicek |
| 5,472,443 A | 12/1995 | Cordis et al. |
| 5,478,351 A | 12/1995 | Meade et al. |
| 5,480,406 A | 1/1996 | Nolan et al. |
| 5,480,409 A | 1/1996 | Riza |
| 5,484,436 A | 1/1996 | Eggers et al. |
| 5,496,312 A | 3/1996 | Klicek |
| 5,496,317 A | 3/1996 | Goble et al. |
| 5,496,347 A | 3/1996 | Hashiguchi et al. |
| 5,499,997 A | 3/1996 | Sharpe et al. |
| 5,509,922 A | 4/1996 | Aranyi et al. |
| 5,514,134 A | 5/1996 | Rydell et al. |
| 5,527,313 A | 6/1996 | Scott et al. |
| 5,528,833 A | 6/1996 | Sakuma |
| 5,529,067 A | 6/1996 | Larsen et al. |
| 5,531,744 A | 7/1996 | Nardella et al. |
| 5,536,251 A | 7/1996 | Evard et al. |
| 5,540,684 A | 7/1996 | Hassler, Jr. |
| 5,540,685 A | 7/1996 | Parins et al. |
| 5,540,706 A | 7/1996 | Aust et al. |
| 5,540,715 A | 7/1996 | Katsaros et al. |
| 5,542,945 A | 8/1996 | Fritzsch |
| 5,558,671 A | 9/1996 | Yates |
| 5,558,672 A | 9/1996 | Edwards et al. |
| 5,562,619 A | 10/1996 | Mirarchi et al. |
| 5,562,699 A | 10/1996 | Heimberger et al. |
| 5,562,720 A | 10/1996 | Stern et al. |
| 5,564,615 A | 10/1996 | Bishop et al. |
| 5,569,241 A | 10/1996 | Edwardds |
| 5,569,243 A | 10/1996 | Kortenbach et al. |
| 5,571,100 A | 11/1996 | Goble et al. |
| 5,573,424 A | 11/1996 | Poppe |
| 5,573,534 A | 11/1996 | Stone |
| 5,573,535 A | 11/1996 | Viklund |
| 5,575,799 A | 11/1996 | Bolanos et al. |
| 5,575,805 A | 11/1996 | Li |
| 5,578,052 A | 11/1996 | Koros et al. |
| 5,579,781 A | 12/1996 | Cooke |
| 5,582,611 A | 12/1996 | Tsukagoshi et al. |
| 5,582,617 A | 12/1996 | Klieman et al. |
| 5,585,896 A | 12/1996 | Yamazaki et al. |
| 5,590,570 A | 1/1997 | LeMaire, III et al. |
| 5,591,181 A | 1/1997 | Stone et al. |
| 5,597,107 A | 1/1997 | Knodel et al. |
| 5,601,224 A | 2/1997 | Bishop et al. |
| 5,601,601 A | 2/1997 | Tal et al. |
| 5,601,641 A | 2/1997 | Stephens |
| 5,603,711 A | 2/1997 | Parins et al. |
| 5,603,723 A | 2/1997 | Aranyi et al. |
| 5,611,798 A | 3/1997 | Eggers |
| 5,611,808 A | 3/1997 | Hossain et al. |
| 5,611,813 A | 3/1997 | Lichtman |
| 5,620,415 A | 4/1997 | Lucey et al. |
| 5,620,453 A | 4/1997 | Nallakrishnan |
| 5,620,459 A | 4/1997 | Lichtman |
| 5,624,452 A | 4/1997 | Yates |
| 5,626,578 A | 5/1997 | Tihon |
| 5,626,609 A | 5/1997 | Zvenyatsky et al. |
| 5,630,833 A | 5/1997 | Katsaros et al. |
| 5,637,110 A | 6/1997 | Pennybacker et al. |
| 5,638,003 A | 6/1997 | Hall |
| 5,643,294 A | 7/1997 | Tovey et al. |
| 5,647,869 A | 7/1997 | Goble et al. |
| 5,647,871 A | 7/1997 | Levine et al. |
| 5,649,959 A | 7/1997 | Hannam et al. |
| 5,655,650 A | 8/1997 | Naitou |
| 5,658,281 A | 8/1997 | Heard |
| D384,413 S | 9/1997 | Zlock et al. |
| 5,662,667 A | 9/1997 | Knodel |
| 5,665,100 A | 9/1997 | Yoon |
| 5,667,526 A | 9/1997 | Levin |
| 5,674,220 A | 10/1997 | Fox et al. |
| 5,674,229 A | 10/1997 | Tovey et al. |
| 5,681,282 A | 10/1997 | Eggers et al. |
| 5,688,270 A | 11/1997 | Yates et al. |
| 5,690,652 A | 11/1997 | Wurster et al. |
| 5,690,653 A | 11/1997 | Richardson et al. |
| 5,693,051 A | 12/1997 | Schulze et al. |
| 5,693,920 A | 12/1997 | Maeda |
| 5,695,522 A | 12/1997 | LeMaire, III et al. |
| 5,700,261 A | 12/1997 | Brinkerhoff |
| 5,700,270 A | 12/1997 | Peyser et al. |
| 5,702,390 A | 12/1997 | Austin et al. |
| 5,707,369 A | 1/1998 | Vaitekunas et al. |
| 5,709,680 A | 1/1998 | Yates et al. |
| 5,716,366 A | 2/1998 | Yates |
| 5,720,744 A | 2/1998 | Eggleston et al. |
| 5,722,421 A | 3/1998 | Francese et al. |
| 5,725,536 A | 3/1998 | Oberlin et al. |
| 5,727,428 A | 3/1998 | LeMaire, III et al. |
| 5,735,848 A | 4/1998 | Yates et al. |
| 5,743,906 A | 4/1998 | Parins et al. |
| 5,752,973 A | 5/1998 | Kieturakis |
| 5,755,717 A | 5/1998 | Yates et al. |
| 5,759,188 A | 6/1998 | Yoon |

| | | | | | | |
|---|---|---|---|---|---|---|
| 5,766,130 A | 6/1998 | Selmonosky | | 5,960,544 A | 10/1999 | Beyers |
| 5,766,166 A | 6/1998 | Hooven | | 5,961,514 A | 10/1999 | Long et al. |
| 5,766,170 A | 6/1998 | Eggers | | 5,964,758 A | 10/1999 | Dresden |
| 5,766,196 A | 6/1998 | Griffiths | | 5,976,132 A | 11/1999 | Morris |
| 5,769,849 A | 6/1998 | Eggers | | 5,984,932 A | 11/1999 | Yoon |
| 5,772,655 A | 6/1998 | Bauer et al. | | 5,984,938 A | 11/1999 | Yoon |
| 5,772,670 A | 6/1998 | Brosa | | 5,984,939 A | 11/1999 | Yoon |
| 5,776,128 A | 7/1998 | Eggers | | 5,989,277 A | 11/1999 | LeMaire, III et al. |
| 5,776,130 A | 7/1998 | Buysse et al. | | 5,993,466 A | 11/1999 | Yoon |
| 5,779,646 A | 7/1998 | Koblish et al. | | 5,993,467 A | 11/1999 | Yoon |
| 5,779,701 A | 7/1998 | McBrayer et al. | | 5,997,565 A | 12/1999 | Inoue |
| H1745 H | 8/1998 | Paraschac | | 6,004,332 A | 12/1999 | Yoon et al. |
| 5,792,137 A | 8/1998 | Carr et al. | | 6,004,335 A | 12/1999 | Vaitekunas et al. |
| 5,792,165 A | 8/1998 | Klieman et al. | | 6,010,516 A | 1/2000 | Hulka et al. |
| 5,792,177 A | 8/1998 | Kaseda | | 6,017,358 A | 1/2000 | Yoon et al. |
| 5,797,537 A | 8/1998 | Oberlin et al. | | 6,021,693 A | 2/2000 | Feng-Sing |
| 5,797,927 A | 8/1998 | Yoon | | 6,024,741 A | 2/2000 | Williamson et al. |
| 5,797,938 A | 8/1998 | Paraschac et al. | | 6,024,743 A | 2/2000 | Edwards |
| 5,797,941 A | 8/1998 | Schulze et al. | | 6,024,744 A | 2/2000 | Kese et al. |
| 5,797,958 A | 8/1998 | Yoon | | 6,027,522 A | 2/2000 | Palmer |
| 5,800,449 A | 9/1998 | Wales | | 6,030,384 A | 2/2000 | Nezhat |
| 5,807,393 A | 9/1998 | Williamson, IV et al. | | 6,033,399 A | 3/2000 | Gines |
| 5,810,764 A | 9/1998 | Eggers et al. | | 6,039,733 A | 3/2000 | Buysse et al. |
| 5,810,805 A | 9/1998 | Sutcu et al. | | 6,041,679 A | 3/2000 | Slater et al. |
| 5,810,808 A | 9/1998 | Eggers | | 6,050,996 A | 4/2000 | Schmaltz et al. |
| 5,810,811 A | 9/1998 | Yates et al. | | 6,053,914 A | 4/2000 | Eggers et al. |
| 5,810,877 A | 9/1998 | Roth et al. | | 6,053,933 A | 4/2000 | Balazs et al. |
| 5,814,043 A | 9/1998 | Shapeton | | D424,694 S | 5/2000 | Tetzlaff et al. |
| 5,814,054 A | 9/1998 | Kortenbach et al. | | D425,201 S | 5/2000 | Tetzlaff et al. |
| 5,817,093 A | 10/1998 | Williamson, IV et al. | | 6,059,782 A | 5/2000 | Novak et al. |
| 5,817,119 A | 10/1998 | Klieman et al. | | 6,066,139 A | 5/2000 | Ryan et al. |
| 5,820,630 A | 10/1998 | Lind | | 6,074,386 A | 6/2000 | Goble et al. |
| 5,824,978 A | 10/1998 | Karasik et al. | | 6,077,287 A | 6/2000 | Taylor et al. |
| 5,827,271 A | 10/1998 | Buysse et al. | | 6,080,180 A | 6/2000 | Yoon et al. |
| 5,827,279 A | 10/1998 | Hughett et al. | | RE36,795 E | 7/2000 | Rydell |
| 5,827,281 A | 10/1998 | Levin | | 6,083,223 A | 7/2000 | Baker |
| 5,827,323 A | 10/1998 | Klieman et al. | | 6,086,586 A | 7/2000 | Hooven |
| 5,827,548 A | 10/1998 | Lavallee et al. | | 6,086,601 A | 7/2000 | Yoon |
| 5,833,690 A | 11/1998 | Yates et al. | | 6,090,107 A | 7/2000 | Borgmeier et al. |
| 5,843,080 A | 12/1998 | Fleenor et al. | | 6,096,037 A | 8/2000 | Mulier et al. |
| 5,849,022 A | 12/1998 | Sakashita et al. | | 6,099,550 A | 8/2000 | Yoon |
| 5,853,412 A | 12/1998 | Mayenberger | | 6,102,909 A | 8/2000 | Chen et al. |
| 5,859,527 A | 1/1999 | Cook | | 6,106,542 A | 8/2000 | Toybin et al. |
| 5,860,976 A | 1/1999 | Billings et al. | | 6,110,171 A | 8/2000 | Rydell |
| 5,876,401 A | 3/1999 | Schulze et al. | | 6,113,596 A | 9/2000 | Hooven et al. |
| 5,876,412 A | 3/1999 | Piraka | | 6,113,598 A | 9/2000 | Baker |
| 5,882,567 A | 3/1999 | Cavallaro et al. | | 6,117,158 A | 9/2000 | Measamer et al. |
| 5,891,141 A | 4/1999 | Rydell | | 6,122,549 A | 9/2000 | Sharkey et al. |
| 5,891,142 A | 4/1999 | Eggers et al. | | 6,123,701 A | 9/2000 | Nezhat |
| 5,893,863 A | 4/1999 | Yoon | | H1904 H | 10/2000 | Yates et al. |
| 5,893,875 A | 4/1999 | O'Connor et al. | | 6,126,658 A | 10/2000 | Baker |
| 5,893,877 A | 4/1999 | Gampp, Jr. et al. | | 6,126,665 A | 10/2000 | Yoon |
| 5,897,563 A | 4/1999 | Yoon et al. | | 6,139,563 A | 10/2000 | Cosgrove, III et al. |
| 5,902,301 A | 5/1999 | Olig | | 6,143,005 A | 11/2000 | Yoon et al. |
| 5,906,630 A | 5/1999 | Anderhub et al. | | 6,152,923 A | 11/2000 | Ryan |
| 5,908,420 A | 6/1999 | Parins et al. | | 6,162,220 A | 12/2000 | Nezhat |
| 5,908,432 A | 6/1999 | Pan | | 6,171,316 B1 | 1/2001 | Kovac et al. |
| 5,911,719 A | 6/1999 | Eggers | | 6,174,309 B1 | 1/2001 | Wrublewski et al. |
| 5,913,874 A | 6/1999 | Berns et al. | | 6,178,628 B1 | 1/2001 | Clemens et al. |
| 5,921,916 A | 7/1999 | Aeikens et al. | | 6,179,834 B1 | 1/2001 | Buysse et al. |
| 5,921,984 A | 7/1999 | Sutcu et al. | | 6,179,837 B1 | 1/2001 | Hooven |
| 5,925,043 A | 7/1999 | Kumar et al. | | 6,183,467 B1 | 2/2001 | Shapeton et al. |
| 5,928,136 A | 7/1999 | Barry | | 6,187,003 B1 | 2/2001 | Buysse et al. |
| 5,935,126 A | 8/1999 | Riza | | 6,190,386 B1 | 2/2001 | Rydell |
| 5,941,869 A | 8/1999 | Patterson et al. | | 6,190,400 B1 | 2/2001 | VanDeMoer et al. |
| 5,944,718 A | 8/1999 | Austin et al. | | 6,193,718 B1 | 2/2001 | Kortenbach et al. |
| 5,951,546 A | 9/1999 | Lorentzen | | 6,206,876 B1 | 3/2001 | Levine et al. |
| 5,951,549 A | 9/1999 | Richardson et al. | | 6,206,877 B1 | 3/2001 | Kese et al. |
| 5,954,720 A | 9/1999 | Wilson et al. | | 6,206,893 B1 | 3/2001 | Klein et al. |
| 5,954,731 A | 9/1999 | Yoon | | 6,214,028 B1 | 4/2001 | Yoon et al. |
| 5,954,733 A | 9/1999 | Yoon | | 6,217,602 B1 | 4/2001 | Redmon |
| 5,957,923 A | 9/1999 | Hahnen et al. | | 6,217,615 B1 | 4/2001 | Sioshansi et al. |
| 5,957,937 A | 9/1999 | Yoon | | 6,221,039 B1 | 4/2001 | Durgin et al. |

| | | | | | | |
|---|---|---|---|---|---|---|
| 6,223,100 B1 | 4/2001 | Green | | 6,605,790 B2 | 8/2003 | Yoshida |
| 6,224,593 B1 | 5/2001 | Ryan et al. | | 6,616,658 B2 | 9/2003 | Ineson |
| 6,224,614 B1 | 5/2001 | Yoon | | 6,616,661 B2 | 9/2003 | Wellman et al. |
| 6,228,080 B1 | 5/2001 | Gines | | 6,620,161 B2 | 9/2003 | Schulze et al. |
| 6,228,083 B1 | 5/2001 | Lands et al. | | 6,620,184 B2 | 9/2003 | de Laforcade et al. |
| 6,248,124 B1 | 6/2001 | Pedros et al. | | 6,626,901 B1 | 9/2003 | Treat et al. |
| 6,248,944 B1 | 6/2001 | Ito | | 6,638,287 B2 | 10/2003 | Danitz et al. |
| 6,261,307 B1 | 7/2001 | Yoon et al. | | 6,641,595 B1 | 11/2003 | Moran et al. |
| 6,267,761 B1 | 7/2001 | Ryan | | 6,652,514 B2 | 11/2003 | Ellman et al. |
| 6,270,497 B1 | 8/2001 | Sekino et al. | | 6,652,521 B2 | 11/2003 | Schulze |
| 6,270,508 B1 | 8/2001 | Klieman et al. | | 6,656,175 B2 | 12/2003 | Francischelli et al. |
| 6,273,887 B1 | 8/2001 | Yamauchi et al. | | 6,656,177 B2 | 12/2003 | Truckai et al. |
| 6,277,117 B1 | 8/2001 | Tetzlaff et al. | | 6,660,072 B2 | 12/2003 | Chatterjee |
| 6,280,458 B1 | 8/2001 | Boche et al. | | 6,663,639 B1 | 12/2003 | Laufer et al. |
| 6,283,961 B1 | 9/2001 | Underwood et al. | | 6,663,641 B1 | 12/2003 | Kovac et al. |
| D449,886 S | 10/2001 | Tetzlaff et al. | | 6,666,854 B1 | 12/2003 | Lange |
| 6,298,550 B1 | 10/2001 | Kirwan | | 6,669,696 B2 | 12/2003 | Bacher et al. |
| 6,302,424 B1 | 10/2001 | Gisinger et al. | | 6,673,092 B1 | 1/2004 | Bacher |
| 6,319,262 B1 | 11/2001 | Bates et al. | | 6,676,660 B2 | 1/2004 | Wampler et al. |
| 6,319,451 B1 | 11/2001 | Brune | | 6,676,676 B2 | 1/2004 | Danitz et al. |
| 6,322,561 B1 | 11/2001 | Eggers et al. | | 6,679,882 B1 | 1/2004 | Kornerup |
| 6,322,580 B1 | 11/2001 | Kanner | | 6,682,527 B2 | 1/2004 | Strul |
| 6,325,795 B1 | 12/2001 | Lindemann et al. | | 6,682,528 B2 | 1/2004 | Frazier et al. |
| 6,334,860 B1 | 1/2002 | Dorn | | 6,685,724 B1 | 2/2004 | Haluck |
| 6,334,861 B1 | 1/2002 | Chandler et al. | | 6,689,131 B2 | 2/2004 | McClurken |
| 6,345,532 B1 | 2/2002 | Coudray et al. | | 6,692,445 B2 | 2/2004 | Roberts et al. |
| 6,350,264 B1 | 2/2002 | Hooven | | 6,693,246 B1 | 2/2004 | Rudolph et al. |
| 6,352,536 B1 | 3/2002 | Buysse et al. | | 6,695,840 B2 | 2/2004 | Schulze |
| 6,358,249 B1 | 3/2002 | Chen et al. | | 6,702,810 B2 | 3/2004 | McClurken et al. |
| 6,358,259 B1 | 3/2002 | Swain et al. | | 6,723,092 B2 * | 4/2004 | Brown et al. .................. 606/41 |
| 6,358,268 B1 | 3/2002 | Hunt et al. | | 6,726,068 B2 | 4/2004 | Miller |
| 6,364,879 B1 | 4/2002 | Chen et al. | | 6,726,686 B2 | 4/2004 | Buysse et al. |
| D457,958 S | 5/2002 | Dycus et al. | | 6,726,694 B2 | 4/2004 | Blatter et al. |
| D457,959 S | 5/2002 | Tetzlaff et al. | | 6,733,498 B2 | 5/2004 | Paton et al. |
| 6,387,094 B1 | 5/2002 | Eitenmuller | | 6,736,813 B2 | 5/2004 | Yamauchi et al. |
| 6,391,035 B1 | 5/2002 | Appleby et al. | | 6,743,229 B2 | 6/2004 | Buysse et al. |
| 6,398,779 B1 | 6/2002 | Buysse et al. | | 6,743,230 B2 | 6/2004 | Lutze et al. |
| 6,402,747 B1 | 6/2002 | Lindemann et al. | | 6,743,239 B1 | 6/2004 | Kuehn et al. |
| 6,409,728 B1 | 6/2002 | Ehr et al. | | 6,743,240 B2 | 6/2004 | Smith et al. |
| H2037 H | 7/2002 | Yates et al. | | 6,755,843 B2 | 6/2004 | Chung et al. |
| 6,419,675 B1 | 7/2002 | Gallo, Sr. | | 6,756,553 B1 | 6/2004 | Yamaguchi et al. |
| 6,425,896 B1 | 7/2002 | Baltschun et al. | | 6,757,977 B2 | 7/2004 | Dambal et al. |
| 6,432,112 B2 | 8/2002 | Brock et al. | | D493,888 S | 8/2004 | Reschke |
| 6,440,144 B1 | 8/2002 | Bacher | | 6,770,072 B2 | 8/2004 | Truckai et al. |
| 6,443,952 B1 | 9/2002 | Mulier et al. | | 6,773,409 B2 | 8/2004 | Truckai et al. |
| 6,443,970 B1 | 9/2002 | Schulze et al. | | 6,773,432 B1 | 8/2004 | Clayman et al. |
| 6,451,018 B1 | 9/2002 | Lands et al. | | 6,773,434 B2 | 8/2004 | Ciarrocca |
| 6,458,125 B1 | 10/2002 | Cosmescu | | 6,773,441 B1 | 8/2004 | Laufer et al. |
| 6,458,128 B1 | 10/2002 | Schulze | | 6,775,575 B2 | 8/2004 | Bommannan et al. |
| 6,458,130 B1 | 10/2002 | Frazier et al. | | 6,776,780 B2 | 8/2004 | Mulier et al. |
| 6,461,352 B2 | 10/2002 | Morgan et al. | | 6,786,905 B2 | 9/2004 | Swanson et al. |
| 6,461,368 B2 | 10/2002 | Fogarty et al. | | 6,790,217 B2 | 9/2004 | Schulze et al. |
| 6,464,701 B1 | 10/2002 | Hooven et al. | | 6,796,981 B2 | 9/2004 | Wham et al. |
| 6,464,702 B2 | 10/2002 | Schulze et al. | | D496,997 S | 10/2004 | Dycus et al. |
| 6,464,704 B2 | 10/2002 | Schmaltz et al. | | 6,800,825 B1 | 10/2004 | Sasaki et al. |
| 6,485,489 B2 | 11/2002 | Teirstein et al. | | 6,802,843 B2 | 10/2004 | Truckai et al. |
| 6,494,888 B1 | 12/2002 | Laufer et al. | | 6,808,525 B2 | 10/2004 | Latterell et al. |
| 6,500,176 B1 | 12/2002 | Truckai et al. | | D499,181 S | 11/2004 | Dycus et al. |
| 6,506,196 B1 | 1/2003 | Laufer | | 6,818,000 B2 | 11/2004 | Muller et al. |
| 6,508,815 B1 | 1/2003 | Strul et al. | | 6,821,285 B2 | 11/2004 | Laufer et al. |
| 6,511,480 B1 | 1/2003 | Tetzlaff et al. | | 6,835,200 B2 | 12/2004 | Laufer et al. |
| 6,514,215 B1 | 2/2003 | Ouchi | | 6,857,357 B2 | 2/2005 | Fujii |
| 6,514,252 B2 | 2/2003 | Nezhat et al. | | 6,860,880 B2 | 3/2005 | Treat et al. |
| 6,517,539 B1 | 2/2003 | Smith et al. | | 6,887,240 B1 | 5/2005 | Lands et al. |
| 6,527,771 B1 | 3/2003 | Weadock et al. | | 6,889,116 B2 | 5/2005 | Jinno |
| 6,533,784 B2 | 3/2003 | Truckai et al. | | 6,914,201 B2 | 7/2005 | Van Vooren et al. |
| 6,545,239 B2 | 4/2003 | Spedale et al. | | 6,926,716 B2 | 8/2005 | Baker et al. |
| 6,558,385 B1 | 5/2003 | McClurken et al. | | 6,929,644 B2 | 8/2005 | Truckai et al. |
| 6,562,037 B2 | 5/2003 | Paton et al. | | 6,932,810 B2 | 8/2005 | Ryan |
| 6,569,105 B1 | 5/2003 | Kortenbach et al. | | 6,932,816 B2 | 8/2005 | Phan |
| 6,582,450 B2 | 6/2003 | Ouchi | | 6,934,134 B2 | 8/2005 | Mori et al. |
| 6,585,735 B1 | 7/2003 | Frazier et al. | | 6,936,061 B2 | 8/2005 | Sasaki |
| 6,602,252 B2 | 8/2003 | Mollenauer | | D509,297 S | 9/2005 | Wells |

| | | | | | | |
|---|---|---|---|---|---|---|
| 6,942,662 B2 | 9/2005 | Goble et al. | 7,248,944 B2 | 7/2007 | Green | |
| 6,943,311 B2 | 9/2005 | Miyako | 7,252,667 B2 | 8/2007 | Moses et al. | |
| 6,953,430 B2 | 10/2005 | Kodooka | 7,255,697 B2 | 8/2007 | Dycus et al. | |
| 6,953,461 B2 | 10/2005 | McClurken et al. | 7,267,677 B2 | 9/2007 | Johnson et al. | |
| 6,958,070 B2 | 10/2005 | Witt et al. | 7,270,660 B2 | 9/2007 | Ryan | |
| 6,960,210 B2 | 11/2005 | Lands et al. | 7,270,664 B2 | 9/2007 | Johnson et al. | |
| 6,964,662 B2 | 11/2005 | Kidooka | 7,276,068 B2 | 10/2007 | Johnson et al. | |
| 6,966,907 B2 | 11/2005 | Goble | 7,300,435 B2 | 11/2007 | Wham et al. | |
| 6,972,017 B2 | 12/2005 | Smith et al. | 7,303,557 B2 | 12/2007 | Wham et al. | |
| 6,977,495 B2 | 12/2005 | Donofrio | 7,311,709 B2 | 12/2007 | Truckai et al. | |
| 6,979,786 B2 | 12/2005 | Aukland et al. | 7,314,471 B2 | 1/2008 | Holman | |
| 6,981,628 B2 | 1/2006 | Wales | 7,318,823 B2 | 1/2008 | Sharps et al. | |
| 6,987,244 B2 | 1/2006 | Bauer | 7,329,256 B2 | 2/2008 | Johnson et al. | |
| 6,994,707 B2 | 2/2006 | Ellman et al. | 7,329,257 B2 * | 2/2008 | Kanehira et al. | 606/52 |
| 6,994,709 B2 | 2/2006 | Iida | D564,662 S | 3/2008 | Moses et al. | |
| 6,997,931 B2 | 2/2006 | Sauer et al. | 7,338,526 B2 | 3/2008 | Steinberg | |
| 7,001,381 B2 | 2/2006 | Harano et al. | 7,342,754 B2 | 3/2008 | Fitzgerald et al. | |
| 7,011,657 B2 | 3/2006 | Truckai et al. | 7,344,268 B2 | 3/2008 | Jigamian | |
| 7,033,354 B2 | 4/2006 | Keppel | D567,943 S | 4/2008 | Moses et al. | |
| 7,033,356 B2 | 4/2006 | Latterell et al. | 7,367,976 B2 | 5/2008 | Lawes et al. | |
| 7,041,102 B2 | 5/2006 | Truckai et al. | 7,377,920 B2 | 5/2008 | Buysse et al. | |
| 7,044,948 B2 | 5/2006 | Keppel | 7,384,420 B2 | 6/2008 | Dycus et al. | |
| 7,052,489 B2 | 5/2006 | Griego et al. | 7,384,421 B2 | 6/2008 | Hushka | |
| 7,052,496 B2 | 5/2006 | Yamauchi | 7,396,336 B2 | 7/2008 | Orszulak et al. | |
| 7,063,715 B2 | 6/2006 | Onuki et al. | D575,395 S | 8/2008 | Hushka | |
| D525,361 S | 7/2006 | Hushka | D575,401 S | 8/2008 | Hixson et al. | |
| 7,070,597 B2 | 7/2006 | Truckai et al. | 7,435,249 B2 | 10/2008 | Buysse et al. | |
| 7,083,618 B2 | 8/2006 | Couture et al. | 7,442,193 B2 | 10/2008 | Shields et al. | |
| 7,083,619 B2 | 8/2006 | Truckai et al. | 7,442,194 B2 | 10/2008 | Dumbauld et al. | |
| 7,083,620 B2 | 8/2006 | Jahns et al. | 7,445,621 B2 | 11/2008 | Dumbauld et al. | |
| 7,087,051 B2 | 8/2006 | Bourne et al. | 7,458,972 B2 | 12/2008 | Keppel | |
| 7,087,054 B2 | 8/2006 | Truckai et al. | 7,473,253 B2 | 1/2009 | Dycus et al. | |
| 7,090,673 B2 | 8/2006 | Dycus et al. | 7,481,810 B2 | 1/2009 | Dumbauld et al. | |
| 7,090,689 B2 | 8/2006 | Nagase et al. | 7,487,780 B2 | 2/2009 | Hooven | |
| 7,101,371 B2 | 9/2006 | Dycus et al. | 7,491,201 B2 | 2/2009 | Shields et al. | |
| 7,101,372 B2 | 9/2006 | Dycus et al. | 7,491,202 B2 | 2/2009 | Odom et al. | |
| 7,101,373 B2 | 9/2006 | Dycus et al. | 7,500,975 B2 | 3/2009 | Cunningham et al. | |
| 7,103,947 B2 | 9/2006 | Sartor et al. | 7,510,556 B2 | 3/2009 | Nguyen et al. | |
| 7,107,124 B2 | 9/2006 | Green | 7,513,898 B2 | 4/2009 | Johnson et al. | |
| 7,112,199 B2 | 9/2006 | Cosmescu | 7,540,872 B2 | 6/2009 | Schechter et al. | |
| D531,311 S | 10/2006 | Guerra et al. | 7,549,995 B2 | 6/2009 | Schultz | |
| 7,115,123 B2 | 10/2006 | Knowlton et al. | 7,553,312 B2 | 6/2009 | Tetzlaff et al. | |
| 7,118,570 B2 | 10/2006 | Tetzlaff et al. | 2002/0013583 A1 * | 1/2002 | Camran et al. | 606/48 |
| 7,118,587 B2 | 10/2006 | Dycus et al. | 2002/0049442 A1 | 4/2002 | Roberts et al. | |
| 7,131,860 B2 | 11/2006 | Sartor et al. | 2002/0099372 A1 | 7/2002 | Schulze et al. | |
| 7,131,970 B2 | 11/2006 | Moses et al. | 2002/0107517 A1 | 8/2002 | Witt et al. | |
| 7,131,971 B2 | 11/2006 | Dycus et al. | 2002/0111624 A1 | 8/2002 | Witt et al. | |
| 7,135,020 B2 | 11/2006 | Lawes et al. | 2002/0188294 A1 | 12/2002 | Couture et al. | |
| D533,942 S | 12/2006 | Kerr et al. | 2003/0014052 A1 | 1/2003 | Buysse et al. | |
| 7,145,757 B2 | 12/2006 | Shea et al. | 2003/0014053 A1 | 1/2003 | Nguyen et al. | |
| 7,147,638 B2 | 12/2006 | Chapman et al. | 2003/0018331 A1 | 1/2003 | Dycus et al. | |
| 7,150,097 B2 | 12/2006 | Sremcich et al. | 2003/0018332 A1 | 1/2003 | Schmaltz et al. | |
| 7,150,749 B2 | 12/2006 | Dycus et al. | 2003/0032956 A1 | 2/2003 | Lands et al. | |
| 7,153,314 B2 | 12/2006 | Laufer et al. | 2003/0069570 A1 | 4/2003 | Witzel et al. | |
| D535,027 S | 1/2007 | James et al. | 2003/0069571 A1 | 4/2003 | Treat et al. | |
| 7,156,842 B2 | 1/2007 | Sartor et al. | 2003/0078578 A1 | 4/2003 | Truckai et al. | |
| 7,156,846 B2 | 1/2007 | Dycus et al. | 2003/0109875 A1 | 6/2003 | Tetzlaff et al. | |
| 7,160,298 B2 | 1/2007 | Lawes et al. | 2003/0114851 A1 | 6/2003 | Truckai et al. | |
| 7,160,299 B2 | 1/2007 | Baily | 2003/0139741 A1 | 7/2003 | Goble et al. | |
| 7,169,146 B2 | 1/2007 | Truckai et al. | 2003/0139742 A1 | 7/2003 | Wampler et al. | |
| 7,179,255 B2 | 2/2007 | Lettice et al. | 2003/0158548 A1 | 8/2003 | Phan et al. | |
| 7,179,258 B2 | 2/2007 | Buysse et al. | 2003/0158549 A1 | 8/2003 | Swanson | |
| 7,195,631 B2 | 3/2007 | Dumbauld | 2003/0171747 A1 | 9/2003 | Kanehira et al. | |
| D541,418 S | 4/2007 | Schechter et al. | 2003/0181910 A1 | 9/2003 | Dycus et al. | |
| 7,207,990 B2 | 4/2007 | Lands et al. | 2003/0199869 A1 | 10/2003 | Johnson et al. | |
| D541,938 S | 5/2007 | Kerr et al | 2003/0216732 A1 | 11/2003 | Truckai et al. | |
| 7,223,264 B2 | 5/2007 | Daniel et al. | 2003/0220637 A1 | 11/2003 | Truckai et al. | |
| 7,223,265 B2 | 5/2007 | Keppel | 2003/0229344 A1 | 12/2003 | Dycus et al. | |
| 7,232,440 B2 | 6/2007 | Dumbauld et al. | 2003/0236325 A1 | 12/2003 | Bonora | |
| 7,241,288 B2 | 7/2007 | Braun | 2003/0236518 A1 | 12/2003 | Marchitto et al. | |
| 7,241,296 B2 | 7/2007 | Buysse et al. | 2004/0030330 A1 | 2/2004 | Brassell et al. | |
| 7,244,257 B2 | 7/2007 | Podjahsky et al. | 2004/0030332 A1 | 2/2004 | Knowlton et al. | |
| 7,246,734 B2 | 7/2007 | Shelto, IV | 2004/0049185 A1 | 3/2004 | Latterell et al. | |

| | | |
|---|---|---|
| 2004/0064151 A1 | 4/2004 | Mollenauer |
| 2004/0073238 A1 | 4/2004 | Makower |
| 2004/0073256 A1 | 4/2004 | Marchitto et al. |
| 2004/0078035 A1 | 4/2004 | Kanehira et al. |
| 2004/0082952 A1 | 4/2004 | Dycus et al. |
| 2004/0087943 A1 | 5/2004 | Dycus et al. |
| 2004/0115296 A1 | 6/2004 | Duffin |
| 2004/0116924 A1 | 6/2004 | Dycus et al. |
| 2004/0116979 A1 | 6/2004 | Truckai et al. |
| 2004/0122423 A1 | 6/2004 | Dycus et al. |
| 2004/0143263 A1 | 7/2004 | Schechter et al. |
| 2004/0147925 A1 | 7/2004 | Buysse et al. |
| 2004/0148035 A1 | 7/2004 | Barrett et al. |
| 2004/0162557 A1 | 8/2004 | Tetzlaff et al. |
| 2004/0176762 A1 | 9/2004 | Lawes et al. |
| 2004/0193153 A1 | 9/2004 | Sarter et al. |
| 2004/0199181 A1 | 10/2004 | Knodel et al. |
| 2004/0210282 A1 | 10/2004 | Flock et al. |
| 2004/0224590 A1 | 11/2004 | Rawa et al. |
| 2004/0225288 A1 | 11/2004 | Buysse et al. |
| 2004/0230189 A1 | 11/2004 | Keppel |
| 2004/0236325 A1 | 11/2004 | Tetzlaff et al. |
| 2004/0236326 A1 | 11/2004 | Schulze et al. |
| 2004/0243125 A1 | 12/2004 | Dycus et al. |
| 2004/0249371 A1 | 12/2004 | Dycus et al. |
| 2004/0249374 A1 | 12/2004 | Tetzlaff et al. |
| 2004/0250419 A1 | 12/2004 | Sremcich et al. |
| 2004/0254573 A1 | 12/2004 | Dycus et al. |
| 2004/0260281 A1 | 12/2004 | Baxter, III et al. |
| 2005/0004564 A1 | 1/2005 | Wham et al. |
| 2005/0004568 A1 | 1/2005 | Lawes et al. |
| 2005/0004569 A1 | 1/2005 | Witt et al. |
| 2005/0004570 A1 | 1/2005 | Chapman et al. |
| 2005/0021025 A1 | 1/2005 | Buysse et al. |
| 2005/0021026 A1 | 1/2005 | Baily |
| 2005/0021027 A1 | 1/2005 | Shields et al. |
| 2005/0033278 A1 | 2/2005 | McClurken et al. |
| 2005/0059934 A1 | 3/2005 | Wenchell et al. |
| 2005/0096645 A1 | 5/2005 | Wellman et al. |
| 2005/0101951 A1 | 5/2005 | Wham et al. |
| 2005/0101952 A1 | 5/2005 | Lands et al. |
| 2005/0107784 A1 | 5/2005 | Moses et al. |
| 2005/0107785 A1 | 5/2005 | Dycus et al. |
| 2005/0113818 A1 | 5/2005 | Sartor et al. |
| 2005/0113819 A1 | 5/2005 | Wham et al. |
| 2005/0113826 A1 | 5/2005 | Johnson et al. |
| 2005/0113827 A1 | 5/2005 | Dumbauld et al. |
| 2005/0113828 A1 | 5/2005 | Shields et al. |
| 2005/0119655 A1 | 6/2005 | Moses et al. |
| 2005/0149017 A1 | 7/2005 | Dycus |
| 2005/0149151 A1 | 7/2005 | Orszulak et al. |
| 2005/0154387 A1 | 7/2005 | Moses et al. |
| 2005/0187547 A1 | 8/2005 | Sugi |
| 2005/0197659 A1 | 9/2005 | Bahney |
| 2005/0203504 A1 | 9/2005 | Wham et al. |
| 2005/0240179 A1 | 10/2005 | Buysse et al. |
| 2006/0052778 A1 | 3/2006 | Chapman et al. |
| 2006/0052779 A1 | 3/2006 | Hammill |
| 2006/0064085 A1 | 3/2006 | Schechter et al. |
| 2006/0064086 A1 | 3/2006 | Odom |
| 2006/0074417 A1 | 4/2006 | Cunningham et al. |
| 2006/0079888 A1 | 4/2006 | Mulier et al. |
| 2006/0079890 A1 | 4/2006 | Guerra |
| 2006/0079891 A1 | 4/2006 | Arts et al. |
| 2006/0079933 A1 | 4/2006 | Hushka et al. |
| 2006/0084973 A1 | 4/2006 | Hushka |
| 2006/0089670 A1 | 4/2006 | Hushka |
| 2006/0116675 A1 | 6/2006 | McClurken et al. |
| 2006/0129146 A1 | 6/2006 | Dycus et al. |
| 2006/0161150 A1 | 7/2006 | Keppel |
| 2006/0167450 A1 | 7/2006 | Johnson et al. |
| 2006/0167452 A1 | 7/2006 | Moses et al. |
| 2006/0173452 A1 | 8/2006 | Buysse et al. |
| 2006/0189980 A1 | 8/2006 | Johnson et al. |
| 2006/0189981 A1 | 8/2006 | Dycus et al. |
| 2006/0190035 A1 | 8/2006 | Hushka et al. |
| 2006/0217709 A1 | 9/2006 | Couture et al. |
| 2006/0224158 A1 | 10/2006 | Odom et al. |
| 2006/0229666 A1 | 10/2006 | Suzuki et al. |
| 2006/0253126 A1 | 11/2006 | Bjerken et al. |
| 2006/0259036 A1 | 11/2006 | Tetzlaf et al. |
| 2006/0264922 A1 | 11/2006 | Sartor et al. |
| 2006/0264931 A1 | 11/2006 | Chapman et al. |
| 2006/0271038 A1 | 11/2006 | Johnson et al. |
| 2006/0283093 A1 | 12/2006 | Petrovic et al. |
| 2006/0287641 A1 | 12/2006 | Perlin |
| 2007/0016182 A1 | 1/2007 | Lipson et al. |
| 2007/0016187 A1 | 1/2007 | Weinberg et al. |
| 2007/0043352 A1 | 2/2007 | Garrison et al. |
| 2007/0043353 A1 | 2/2007 | Dycus et al. |
| 2007/0055231 A1 | 3/2007 | Dycus et al. |
| 2007/0060919 A1 | 3/2007 | Isaacson et al. |
| 2007/0062017 A1 | 3/2007 | Dycus et al. |
| 2007/0074807 A1 | 4/2007 | Guerra |
| 2007/0078456 A1 | 4/2007 | Dumbauld et al. |
| 2007/0078458 A1 | 4/2007 | Dumbauld et al. |
| 2007/0078459 A1 | 4/2007 | Johnson et al. |
| 2007/0088356 A1 | 4/2007 | Moses et al. |
| 2007/0106295 A1 | 5/2007 | Garrison et al. |
| 2007/0106297 A1 | 5/2007 | Dumbauld et al. |
| 2007/0118111 A1 | 5/2007 | Weinberg |
| 2007/0118115 A1 | 5/2007 | Artale et al. |
| 2007/0142833 A1 | 6/2007 | Dycus et al. |
| 2007/0142834 A1 | 6/2007 | Dumbauld |
| 2007/0156139 A1 | 7/2007 | Schechter et al. |
| 2007/0156140 A1 | 7/2007 | Baily |
| 2007/0173811 A1 | 7/2007 | Couture et al. |
| 2007/0173814 A1 | 7/2007 | Hixson et al. |
| 2007/0179499 A1 | 8/2007 | Garrison |
| 2007/0198011 A1 | 8/2007 | Sugita |
| 2007/0203485 A1 | 8/2007 | Keppel |
| 2007/0213706 A1 | 9/2007 | Dumbauld et al. |
| 2007/0213707 A1 | 9/2007 | Dumbauld et al. |
| 2007/0213708 A1 | 9/2007 | Dumbauld et al. |
| 2007/0213712 A1 | 9/2007 | Buysse et al. |
| 2007/0255279 A1 | 11/2007 | Buysse et al. |
| 2007/0260235 A1 | 11/2007 | Podhajsky |
| 2007/0260238 A1 | 11/2007 | Guerra |
| 2007/0260241 A1 | 11/2007 | Dalla Betta et al. |
| 2007/0260242 A1 | 11/2007 | Dycus et al. |
| 2007/0265616 A1 | 11/2007 | Couture et al. |
| 2008/0004616 A1 | 1/2008 | Patrick |
| 2008/0009860 A1 | 1/2008 | Odom |
| 2008/0015575 A1 | 1/2008 | Odom et al. |
| 2008/0021450 A1 | 1/2008 | Couture |
| 2008/0033428 A1 | 2/2008 | Artale et al. |
| 2008/0039835 A1 | 2/2008 | Johnson et al. |
| 2008/0039836 A1 | 2/2008 | Odom et al. |
| 2008/0045947 A1 | 2/2008 | Johnson et al. |
| 2008/0058802 A1 | 3/2008 | Couture et al. |
| 2008/0082100 A1 | 4/2008 | Orton et al. |
| 2008/0091189 A1 | 4/2008 | Carlton |
| 2008/0114356 A1 | 5/2008 | Johnson et al. |
| 2008/0167651 A1 | 7/2008 | Tetzlaff et al. |
| 2008/0195093 A1 | 8/2008 | Couture et al. |
| 2008/0215051 A1 | 9/2008 | Buysse et al. |
| 2008/0243120 A1 | 10/2008 | Lawes et al. |
| 2008/0249527 A1 | 10/2008 | Couture |
| 2008/0312653 A1 | 12/2008 | Arts et al. |
| 2008/0319442 A1 | 12/2008 | Unger et al. |
| 2009/0012520 A1 | 1/2009 | Hixson et al. |
| 2009/0018535 A1 | 1/2009 | Schechter et al. |
| 2009/0024126 A1 | 1/2009 | Artale et al. |
| 2009/0043304 A1 | 2/2009 | Tetzlaff et al. |
| 2009/0048596 A1 | 2/2009 | Shields et al. |
| 2009/0062794 A1 | 3/2009 | Buysse et al. |

| | | | |
|---|---|---|---|
| 2009/0082766 A1 | 3/2009 | Unger et al. | |
| 2009/0082767 A1 | 3/2009 | Unger et al. | |
| 2009/0082769 A1 | 3/2009 | Unger et al. | |
| 2009/0088738 A1 | 4/2009 | Guerra et al. | |
| 2009/0088739 A1 | 4/2009 | Hushka et al. | |
| 2009/0088740 A1 | 4/2009 | Guerra et al. | |
| 2009/0088741 A1 | 4/2009 | Hushka et al. | |
| 2009/0088744 A1 | 4/2009 | Townsend | |
| 2009/0088745 A1 | 4/2009 | Hushka et al. | |
| 2009/0088746 A1 | 4/2009 | Hushka et al. | |
| 2009/0088747 A1 | 4/2009 | Hushka et al. | |
| 2009/0088748 A1 | 4/2009 | Guerra et al. | |
| 2009/0088749 A1 | 4/2009 | Hushka et al. | |
| 2009/0088750 A1 | 4/2009 | Hushka et al. | |
| 2009/0112206 A1 | 4/2009 | Dumbauld et al. | |
| 2009/0131934 A1 | 5/2009 | Odom et al. | |
| 2009/0149853 A1 | 6/2009 | Shields et al. | |
| 2009/0149854 A1 | 6/2009 | Cunningham et al. | |
| 2009/0171350 A1 | 7/2009 | Dycus et al. | |
| 2009/0171353 A1 | 7/2009 | Johnson et al. | |
| 2009/0182327 A1 | 7/2009 | Unger | |
| 2009/0187188 A1 | 7/2009 | Guerra et al. | |

FOREIGN PATENT DOCUMENTS

| | | |
|---|---|---|
| DE | 2415263 | 10/1975 |
| DE | 2514501 | 10/1976 |
| DE | 2627679 | 1/1977 |
| DE | 3612646 | 4/1987 |
| DE | 8712328 | 3/1988 |
| DE | 4303882 | 8/1994 |
| DE | 4403252 | 8/1995 |
| DE | 19515914 | 7/1996 |
| DE | 29616210 | 1/1997 |
| DE | 19608716 | 4/1997 |
| DE | 19751106 | 5/1998 |
| DE | 19751108 | 5/1999 |
| DE | 19738457 | 1/2009 |
| EP | 0364216 A1 | 4/1990 |
| EP | 0467501 | 1/1992 |
| EP | 518230 A1 | 12/1992 |
| EP | 0 541 930 B1 | 5/1993 |
| EP | 0572131 | 12/1993 |
| EP | 584787 A1 | 3/1994 |
| EP | 0589453 A2 | 3/1994 |
| EP | 0589555 | 3/1994 |
| EP | 0623316 A1 | 11/1994 |
| EP | 0624348 A2 | 11/1994 |
| EP | 0650701 A1 | 5/1995 |
| EP | 0694290 A3 | 3/1996 |
| EP | 0717966 A1 | 6/1996 |
| EP | 0754437 A3 | 3/1997 |
| EP | 0517243 | 9/1997 |
| EP | 853922 A1 | 7/1998 |
| EP | 0875209 A1 | 11/1998 |
| EP | 0878169 A1 | 11/1998 |
| EP | 0887046 A3 | 1/1999 |
| EP | 0923907 A1 | 6/1999 |
| EP | 0986990 A1 | 3/2000 |
| EP | 1034747 A1 | 9/2000 |
| EP | 1034748 A1 | 9/2000 |
| EP | 1025807 A3 | 10/2000 |
| EP | 1034746 A3 | 10/2000 |
| EP | 1050278 A1 | 11/2000 |
| EP | 1053719 A1 | 11/2000 |
| EP | 1053720 A1 | 11/2000 |
| EP | 1055399 A1 | 11/2000 |
| EP | 1055400 A1 | 11/2000 |
| EP | 1080694 A1 | 3/2001 |
| EP | 1082944 A1 | 3/2001 |
| EP | 1159926 A2 | 12/2001 |
| EP | 1177771 | 2/2002 |
| EP | 1301135 A | 4/2003 |
| EP | 1330991 A1 | 7/2003 |
| EP | 1486177 A2 | 6/2004 |
| EP | 1472984 A1 | 11/2004 |
| EP | 0774232 | 1/2005 |
| EP | 1527747 A2 | 5/2005 |
| EP | 1530952 A1 | 5/2005 |
| EP | 1532932 A1 | 5/2005 |
| EP | 1535581 A2 | 6/2005 |
| EP | 1609430 A1 | 12/2005 |
| EP | 1632192 A1 | 3/2006 |
| EP | 1642543 | 4/2006 |
| EP | 1645238 A1 | 4/2006 |
| EP | 1645240 A2 | 4/2006 |
| EP | 1649821 | 4/2006 |
| EP | 1707143 A1 | 10/2006 |
| EP | 1769765 | 4/2007 |
| EP | 1769766 | 4/2007 |
| EP | 1929970 | 6/2008 |
| EP | 1683496 | 12/2008 |
| GB | 623316 | 5/1949 |
| GB | 1490585 | 11/1977 |
| GB | 2214430 A | 6/1989 |
| GB | 2213416 | 8/1989 |
| JP | 501068 | 9/1984 |
| JP | 502328 | 3/1992 |
| JP | 5-5106 | 1/1993 |
| JP | 5-40112 | 2/1993 |
| JP | 06343644 A2 | 12/1994 |
| JP | 07265328 A2 | 10/1995 |
| JP | 08056955 A2 | 3/1996 |
| JP | 08252263 A2 | 10/1996 |
| JP | 09010223 A2 | 1/1997 |
| JP | 11-070124 | 3/1999 |
| JP | 11244298 A2 | 9/1999 |
| JP | 2000-102545 | 4/2000 |
| JP | 2000342599 A2 | 12/2000 |
| JP | 2000350732 A2 | 12/2000 |
| JP | 2001008944 A2 | 1/2001 |
| JP | 2001029356 A2 | 2/2001 |
| JP | 2001128990 A2 | 5/2001 |
| SU | 401367 | 11/1974 |
| WO | WO89/00757 | 1/1989 |
| WO | WO 92/04873 | 4/1992 |
| WO | WO 92/06642 | 4/1992 |
| WO | WO 93/21845 | 11/1993 |
| WO | WO 94/08524 A | 4/1994 |
| WO | WO94/20025 | 9/1994 |
| WO | WO 95/02369 | 1/1995 |
| WO | WO 95/07662 | 3/1995 |
| WO | WO95/07662 | 3/1995 |
| WO | WO95/15124 | 6/1995 |
| WO | WO96/05776 | 2/1996 |
| WO | WO 96/022056 | 7/1996 |
| WO | WO 96/13218 | 9/1996 |
| WO | WO 97/00646 | 1/1997 |
| WO | WO 97/00647 | 1/1997 |
| WO | WO 97/10764 | 3/1997 |
| WO | WO97/10764 | 3/1997 |
| WO | WO 97/24073 | 7/1997 |
| WO | WO 97/24993 | 7/1997 |
| WO | WO 98/27880 | 7/1998 |
| WO | WO 99/03407 | 1/1999 |
| WO | WO 99/03408 | 1/1999 |
| WO | WO 99/03409 | 1/1999 |
| WO | WO 99/12488 | 3/1999 |
| WO | WO 99/23933 | 5/1999 |
| WO | WO 99/40857 | 8/1999 |
| WO | WO 99/040861 | 8/1999 |
| WO | WO 99/51158 | 10/1999 |
| WO | WO 99/66850 | 12/1999 |
| WO | WO 99/66850 A | 12/1999 |
| WO | WO 00/24330 | 5/2000 |
| WO | WO00/24331 | 5/2000 |

| | | |
|---|---|---|
| WO | WO 00/24331 | 5/2000 |
| WO | WO 00/36986 | 6/2000 |
| WO | WO 00/41638 | 7/2000 |
| WO | WO00/47124 | 8/2000 |
| WO | WO 00/53112 | 9/2000 |
| WO | WO 01/17448 A | 3/2001 |
| WO | WO 01/54604 | 8/2001 |
| WO | WO02/07627 | 1/2002 |
| WO | WO 02/07627 | 1/2002 |
| WO | WO 02/067798 A1 | 9/2002 |
| WO | WO 02/080783 | 10/2002 |
| WO | WO02/080783 | 10/2002 |
| WO | WO 02/080784 | 10/2002 |
| WO | WO02/080784 | 10/2002 |
| WO | WO 02/080785 | 10/2002 |
| WO | WO02/080785 | 10/2002 |
| WO | WO02/080786 | 10/2002 |
| WO | WO 02/080786 | 10/2002 |
| WO | WO02/080793 | 10/2002 |
| WO | WO 02/080793 | 10/2002 |
| WO | WO02/080794 | 10/2002 |
| WO | WO 02/080794 | 10/2002 |
| WO | WO 02/080795 | 10/2002 |
| WO | WO 02/080796 | 10/2002 |
| WO | WO02/080797 | 10/2002 |
| WO | WO 02/080797 | 10/2002 |
| WO | WO 02/080798 | 10/2002 |
| WO | WO 02/080799 | 10/2002 |
| WO | WO02/081170 | 10/2002 |
| WO | WO 02/081170 | 10/2002 |
| WO | WO 03/061500 | 7/2003 |
| WO | WO 03/090630 A3 | 11/2003 |
| WO | WO 03/101311 | 12/2003 |
| WO | WO 2004/032776 A1 | 4/2004 |
| WO | WO2004/032777 | 4/2004 |
| WO | WO 2004/032777 | 4/2004 |
| WO | WO 2004/052221 | 6/2004 |
| WO | WO 2004/073488 A2 | 9/2004 |
| WO | WO2004/073490 | 9/2004 |
| WO | WO 2004/073490 | 9/2004 |
| WO | WO2004/073753 | 9/2004 |
| WO | WO 2004/082495 | 9/2004 |
| WO | WO 2004/098383 | 11/2004 |
| WO | WO 2004/103156 | 12/2004 |
| WO | WO 2005/004734 A1 | 1/2005 |
| WO | WO2005/004735 | 1/2005 |
| WO | WO 2005/110264 | 11/2005 |
| WO | WO 2008/045348 | 4/2008 |
| WO | WO 2008/045350 | 4/2008 |

OTHER PUBLICATIONS

Int'l Search Report EP 07 010672.9 dated Oct. 1, 2007.
Int'l Search Report EP 07 013779.9 dated Oct. 18, 2007.
Int'l Search Report EP 07 009026.1 dated Sep. 12, 2007.
Int'l Search Report EP 07 015601.3 dated Dec. 6, 2007.
Int'l Search Report EP 07 015191.5 dated Dec. 19, 2007.
Int'l Search Report EP 07 020283.3 dated Jan. 16, 2008.
Sigel et al. "The Mechanism of Blood Vessel Closure by High Frequency Electrocoagulation" Surgery Gynecology & Obstetrics, Oct. 1965 pp. 823-831.
Bergdahl et al. "Studies on Coagulation and the Development of an Automatic Computerized Bipolar Coagulator" J.Neurosurg, vol. 75, Jul. 1991, pp. 148-151.
Kennedy et al. "High-burst-strength, feedback-controlled bipolar vessel sealing" Surgical Endoscopy (1998) 12: 876-878.
Peterson et al. "Comparison of Healing Process Following Ligation with Sutures and Bipolar Vessel Sealing" Surgical Technology International (2001).
Linehan et al. "A Phase I Study of the LigaSure Vessel Sealing System in Hepatic Surgery" Section of HPB Surger, Washington University School of Medicine, St. Louis MO, Presented at AHPBA, Feb. 2001.
Johnson et al. "Evaluation of the LigaSure Vessel Sealing System in Hemorrhoidectormy" American College of Surgeons (ACS) Clinicla Congress Poster (2000).
Sayfan et al. "Sutureless Closed Hemorrhoidectomy: A New Technique" Annals of Surgery vol. 234 No. 1 Jul. 2001 pp. 21-24.
Heniford et al. "Initial Results with an Electrothermal Bipolar Vessel Sealer" Surgical Endoscopy (2000) 15:799-801.
Heniford et al. "Initial Research and Clinical Results with an Electrothermal Bipolar Vessel Sealer" Oct. 1999.
McLellan et al. "Vessel Sealing for Hemostasis During Pelvic Surgery" Int'l Federation of Gynecology and Obstetrics FIGO World Congress 2000, Washington, D.C.
Crawford at al. "Use of the LigaSure Vessel Sealing System in Urologic Cancer Surger" Grand Rounds in Urology 1999 vol. 1 Issue 4 pp. 10-17.
Rothenberg et al "Use of the LigaSure Vessel Sealing System in Minimally Invasive Surgery in Children" Int'l Pediatric Endosurgery Group (IPEG) 2000.
Palazzo et al. "Randomized clinical trial of Ligasure versus open haemorrhoidectomy" British Journal of Surgery 2002, 89, 154-157.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Chung et al., "Clinical Experience of Sutureless Closed Hemorrhoidectomy with LigaSure" Diseases of the Colon & Rectum vol. 46, No. 1 Jan. 2003.
Strasberg et al., "Use of a Bipolar Vessel-Sealing Device for Parenchymal Transection During Liver Surgery" Journal of Gastrointestinal Surgery, vol. 6, No. 4, Jul./Aug. 2002 pp. 569-574.
Paul G. Horgan, "A Novel Technique for Parenchymal Division During Hepatectomy" The American Journal of Surgery, vol. 181, No. 3, Apr. 2001 pp. 236-237.
Michael Choti, "Abdominoperineal Resection with the LigaSure Vessel Sealing System and LigaSure Atlas 20 cm Open Instrument" Innovations That Work, Jun. 2003.
Craig Johnson, "Use of the LigaSure Vessel Sealing System in Bloodless Hemorrhoidectomy" Innovations That Work, Mar. 2000.
Muller et al., "Extended Left Hemicolectomy Using the LigaSure Vessel Sealing System" Innovations That Work, Sep. 1999.
Herman et al. "Laparoscopic Intestinal Resection With the LigaSure Vessel Sealing System: A Case Report" Innovations That Work, Feb. 2002.
Carus et al., "Initial Experience With The LigaSure Vessel Sealing System in Abdominal Surgery" Innovations That Work, Jun. 2002.
Levy et al. "Randomized Trial of Suture Versus Electrosurgical Bipolar Vessel Sealing in Vaginal Hysterectomy" Obstetrics & Gynecology, vol. 102, No. 1, Jul. 2003.
Levy et al , "Update on Hysterectomy—New Technologies and Techniques" OBG Management, Feb. 2003.
Barbara Levy, "Use of a New Vessel Ligation Device During Vaginal Hysterectomy" FIGO 2000, Washington, D.C.
Sengupta et al., "Use of a Computer-Controlled Bipolar Diathermy System in Radical Prostatectomies and Other Open Urological Surgery" ANZ Journal of Surgery (2001) 71.9 pp. 538-540.
Olsson et al. "Radical Cystectomy in Females" Current Surgical Techniques in Urology, vol. 14, Issue 3, 2001.
Joseph Ortenberg "LigaSure System Used in Laparoscopic 1st and 2nd Stage Orchiopexy" Innovations That Work, Nov. 2002.
Koyle et al. "Laparoscopic Palomo Varicocele Ligation in Children and Adolescents" Pediatric Endosurgery & Innovative Techniques, vol. 6, No. 1, 2002.
Dulemba et al. "Use of a Bipolar Electrothermal Vessel Sealer in Laparoscopically Assisted Vaginal Hysterectomy" Sales/Product Literature; Jan. 2004.
Johnson et al. "Evaluation of a Bipolar electrothermal Vessel Sealing Device in Hemorrhoidectomy" Sales/Product Literature; Jan. 2004.
Int'l Search Report EP 05016399 dated Jan. 5, 2006.
Int'l Search Report EP 06005185.1 dated Apr. 18, 2006.
Int'l Search Report EP 06008779.8 dated Jun. 13, 2006.
Int'l Search Report EP 1683496 dated Jun. 13, 2006.
Int'l Search Report EP 04013772 dated Apr. 1, 2005.

Int'l Search Report EP 05013895 dated Oct. 14, 2005.
Int'l Search Report EP 05017281 dated Nov. 16, 2005.
Int'l Search Report EP 06006716 dated Aug. 4, 2006.
Int'l Search Report PCT/US01/11224 dated Nov. 13, 2001.
Int'l Search Report EP 06014461.5 dated Oct. 20, 2006.
Int'l Search Report EP 06020584.6 dated Jan. 12, 2007.
Int'l Search Report EP 06020583.8 dated Jan. 30, 2007.
Int'l Search Report EP 06020756.0 dated Feb. 5, 2007.
Int'l Search Report EP 06024123.9 dated Feb. 26, 2007.
Sampayan et al, "Multilayer Ultra-High Gradient Insulator Technology" Discharges and Electrical Insulation in Vacuum, 1998. Netherlands Aug. 17-21, 1998; vol. 2, pp. 740-743.
Crouch et al. "A Velocity-Dependent Model for Needle Insertion in Soft Tissue" MICCAI 2005; LNCS 3750 pp. 624-632, Dated: 2005.
Int'l Search Report EP 98957771 dated Aug. 9, 2001.
Int'l Search Report EP 05002671.5 dated Dec. 22, 2008.
Int'l Search Report EP 05002674.9 dated Jan. 16, 2009.
Int'l Search Report EP 05019429.9 dated May 6, 2008.
Int'l Search Report EP 06008515.6 dated Jan. 8, 2009.
Int'l Search Report EP 07 014016 dated Jan. 28, 2008.
Int'l Search Report EP 07 021646.0 dated Jul. 9, 2008.
Int'l Search Report EP 07 021647.8 dated May 2, 2008.
Int'l Search Report EP 08 02692.5 dated Dec. 12, 2008.
Int'l Search Report EP 08 004655.0 dated Jun. 24, 2008.
Int'l Search Report EP 08 006732.5 dated Jul. 29, 2008.
Int'l Search Report EP 08 006917.2 dated Jul. 3, 2008.
Int'l Search Report EP 08 016539.2 dated Jan. 8, 2009.
Int'l Search Report EP 09 152267.2 Dated Jun. 15, 2009.
Int'l Search Report EP 09 152898.4 Dated Jun. 10, 2009.
Int'l Search Report PCT/US98/24281 dated Feb. 22, 1999.
Int'l Search Report PCT/US03/28534 dated Dec. 19, 2003.
Int'l Search Report PCT/US07/021438 dated Apr. 1, 2008.
Int'l Search Report PCT/US07/021440 dated Apr. 8, 2008.
Int'l Search Report PCT/US08/61498 dated Sep. 22, 2008.
Int'l Search Report PCT/US09/032690 dated Jun. 16, 2009.
"Innovations in Electrosurgery" Sales/Product Literature; Dec. 31, 2000.
LigaSure Vessel Sealing System, the Seal of Confidence in General, Gynecologic, Urologic, and Laparaoscopic Surgery Sales/Product Literature; Jan. 2004.
Olsson et al. "Radical Cystectomy in Females" Current Surgical Techniques in Urology, vol. 14, Issue 3, 2001.
Dulemba et al. "Use of a Bipolar Electrothermal Vessel Sealer in Laparoscopically Assisted Vaginal Hysterectomy" Sales Product Literature; Jan. 2004.
Johnson et al. "Evaluation of a Bipolar electrothermal Vessel Sealing Device in Hemorrhoidectomy" Sales Product Literature; Jan. 2004.
Levy et al. "Use of a New Energy-based Vessel Ligation Device During Vaginal Hysterectomy" Int'l Federation of Gynecology and Obstetrics (FIGO) World Congress 1999.
Carbonell et al., "Comparison of theGyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC 2003.
"Reducing Needlestick Injuries in the Operating Room" Sales/Product Literature 2001.
W. Scott Helton, "LigaSure Vessel Sealing System: Revolutionary Hemostasis Product for General Surgery" Sales/Product Literature 1999.

McLellan et al. "Vessel Sealing for Hemostasis During Gynecologic Surgery" Sales/Product Literature 1999.
E. David Crawford "Use of a Novel Vessel Sealing Technology in Management of the Dorsal Veinous Complex" Sales/Product Literature 2000.
Jarrett et al., "Use of the LigaSure Vessel Sealing System for Peri-Hilar Vessels in Laparoscopic Nephrectomy" Sales/Product Literature 2000.
E. David Crawford "Evaluation of a New Vessel Sealing Device in Urologic Cancer Surgery" Sales/Product Literature 2000.
International Search Report PCT/US01/11224 dated Nov. 13, 2001.
International Search Report EP 98958575.7 dated Sep. 20, 2002.
International Search Report EP 04013772 dated Apr. 1, 2005.
International Search Report EP 05013895 dated Oct. 14, 2005.
International Search Report EP 05017281 dated Nov. 16, 2005.
Int'l Search Report EP 05013463.4 dated Sep. 28, 2005.
Int'l Search Report EP 05019130.3 dated Oct. 18, 2005.
Int'l Search Report EP 05020665.5 dated Feb. 16, 2006.
Int'l Search Report EP 05020666.3 dated Feb. 17, 2006.
Int'l Search Report EP 05021779.3 dated Jan. 18, 2006.
Int'l Search Report EP 05021197.8 dated Jan. 31, 2006.
Int'l Search Report EP 05021937.7 dated Jan. 13, 2006.
Int'l Search Report—extended—EP 05021937.7 dated Mar. 6, 2006.
Int'l Search Report EP 05023017.6 dated Feb. 16, 2006.
Int'l Search Report EP 05021780.1 dated Feb. 9, 2006.
Int'l Search Report EP 06002279.5 dated Mar. 22, 2006.
Int'l Search Report EP 04 752343.6 dated Jul. 20, 2007.
Int'l Search Report EP 06 024122.1 dated Mar. 19, 2007.
Int'l Search Report EP 07 001480.8 dated Apr. 12, 2007.
Int'l Search Report EP 07 001488.1 dated May 29, 2007.
Int'l Search Report—Extended EP 07 009029.5 dated Jul. 12, 2007.
Int'l Search Report EP 07 009321.6 dated Aug. 17, 2007.
Levy et al. " Use of a New Energy-based Vessel Ligation Device During Vaginal Hysterectomy" Int'l Federation of Gynecology and Obstetrics (FIGO) World Congress 1999.
Carbonell et al., "Comparison of the Gyrus PlasmaKinetic Sealer and the Valleylab LigaSure Device in the Hemostasis of Small, Medium, and Large-Sized Arteries" Carolinas Laparoscopic and Advanced Surgery Program, Carolinas Medical Center, Charlotte, NC; Date: Aug. 2003.
Int'l Search Report EP 98944778.4 dated Oct. 31, 2000.
Int'l Search Report EP 98958575.7 dated Sep. 20, 2002.
Int'l Search Report EP 04027314.6 dated Mar. 10, 2005.
Int'l Search Report EP 04027479.7 dated Mar. 8, 2005.
Int'l Search Report EP 04027705.5 dated Feb. 3, 2005.
Int'l Search Report EP 04013772.1 dated Apr. 1, 2005.
Int'l Search Report PCT/US98/18640 dated Jan. 29, 1999.
Int'l Search Report PCT/US98/23950 dated Jan. 14, 1999.
Int'l Search Report PCT/US99/24869 dated Feb. 3, 2000.
Int'l Search Report PCT/US01/11218 dated Aug. 14, 2001.
Int'l Search Report PCT/US01/11340 dated Aug. 16, 2001.
Int'l Search Report PCT/US01/11420 dated Oct. 16, 2001.
Int'l Search Report PCT/US02/01890 dated Jul. 25, 2002.
Int'l Search Report PCT/US02/11100 dated Jul. 16, 2002.
Int'l Search Report PCT/USO4/03436 dated Mar. 3, 2005.
Int'l Search Report PCT/USO4/13273 dated Dec. 15, 2004.
Int'l Search Report PCT/USO4/15311dated Jan. 12, 2005.

* cited by examiner

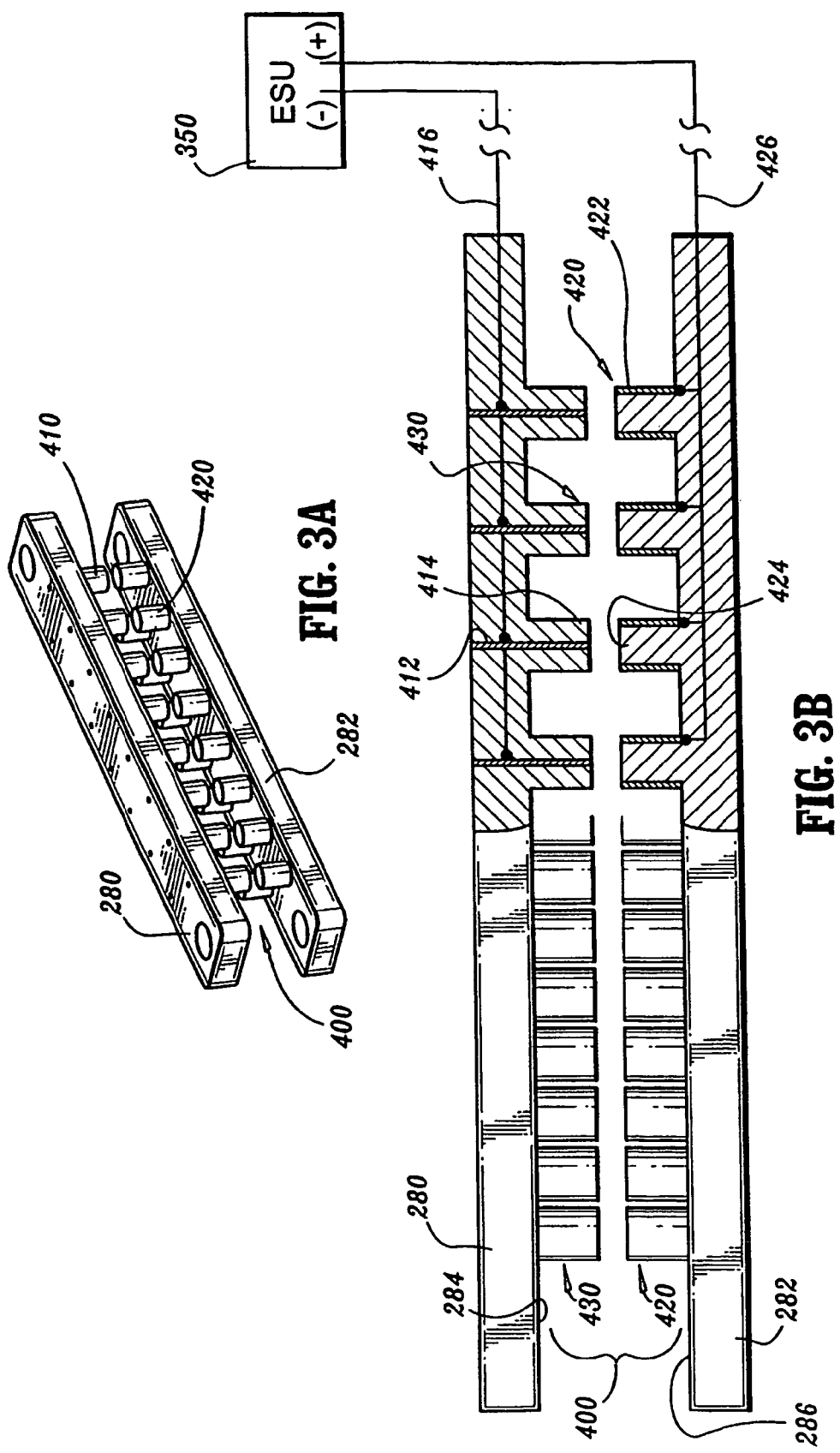

BIPOLAR CONCENTRIC ELECTRODE ASSEMBLY FOR SOFT TISSUE FUSION

BACKGROUND

The present disclosure relates to forceps used for open and/or endoscopic surgical procedures. More particularly, the present disclosure relates to a forceps which applies a unique combination of mechanical clamping pressure and electrosurgical current to micro-seal soft tissue to promote tissue healing.

TECHNICAL FIELD

A hemostat or forceps is a simple plier-like tool which uses mechanical action between its jaws to constrict vessels and is commonly used in open surgical procedures to grasp, dissect and/or clamp tissue. Electrosurgical forceps utilize both mechanical clamping action and electrical energy to effect hemostasis by heating the tissue and blood vessels to coagulate, cauterize and/or seal tissue. The electrode of each opposing jaw member is charged to a different electric potential such that when the jaw members grasp tissue, electrical energy can be selectively transferred through the tissue. A surgeon can either cauterize, coagulate/desiccate and/or simply reduce or slow bleeding, by controlling the intensity, frequency and duration of the electrosurgical energy applied between the electrodes and through the tissue.

For the purposes herein, the term "cauterization" is defined as the use of heat to destroy tissue (also called "diathermy" or "electrodiathermy"). The term "coagulation" is defined as a process of desiccating tissue wherein the tissue cells are ruptured and dried. "Vessel sealing" is defined as the process of liquefying the collagen, elastin and ground substances in the tissue so that it reforms into a fused mass with significantly-reduced demarcation between the opposing tissue structures (opposing walls of the lumen). Coagulation of small vessels is usually sufficient to permanently close them. Larger vessels or tissue need to be sealed to assure permanent closure.

Commonly-owned U.S. Application Serial Nos. PCT Application Ser. No. PCT/US01/11340 filed on Apr. 6, 2001 by Dycus, et al. entitled "VESSEL SEALER AND DIVIDER", U.S. application Ser. No. 10/116,824 filed on Apr. 5, 2002 by Tetzlaff et al. entitled "VESSEL SEALING INSTRUMENT" and PCT Application Serial . No. PCT/US01/11420 filed on Apr. 6, 2001 by Tetzlaff et al. entitled "VESSEL SEALING INSTRUMENT" teach that to effectively seal tissue or vessels, especially large vessels, two predominant mechanical parameters must be accurately controlled: 1) the pressure applied to the vessel; and 2) the gap distance between the conductive tissue contacting surfaces (electrodes). As can be appreciated, both of these parameters are affected by the thickness of the vessel or tissue being sealed. Accurate application of pressure is important for several reasons: to oppose the walls of the vessel; to reduce the tissue impedance to a low enough value that allows enough electrosurgical energy through the tissue; to overcome the forces of expansion during tissue heating; and to contribute to the end tissue thickness which is an indication of a good seal. It has been determined that a typical sealed vessel wall is optimum between 0.001 inches and 0.006 inches. Below this range, the seal may shred or tear and above this range the lumens may not be properly or effectively sealed.

With respect to smaller vessels, the pressure applied become less relevant and the gap distance between the electrically conductive surfaces becomes more significant for effective sealing. In other words, the chances of the two electrically conductive surfaces touching during activation increases as the tissue thickness and the vessels become smaller.

As can be appreciated, when cauterizing, coagulating or sealing vessels, the tissue disposed between the two opposing jaw members is essentially destroyed (e.g., heated, ruptured and/or dried with cauterization and coagulation and fused into a single mass with vessel sealing). Other known electrosurgical instruments include blade members or shearing members which simply cut tissue in a mechanical and/or electromechanical manner and, as such, also destroy tissue viability.

When trying to electrosurgically treat large, soft tissues (e.g., lung, intestine, lymph ducts, etc.) to promote healing, the above-identified surgical treatments are generally impractical due to the fact that in each instance the tissue or a significant portion thereof is essentially destroyed to create the desired surgical effect, cauterization, coagulation and/or sealing. As a result thereof, the tissue is no longer viable across the treatment site, i.e., there remains no feasible path across the tissue for vascularization.

Thus, a need exists to develop an electrosurgical forceps which effectively treats tissue while maintaining tissue viability across the treatment area to promote tissue healing.

SUMMARY

The present disclosure relates to a bipolar electrosurgical forceps for treating tissue and includes a pair of opposing first and second jaw members each having a tissue engaging surface disposed thereon. The opposing jaw members are movable relative to one another from a first position to approximate tissue to a second position for engaging tissue between the jaw members. At least one of the first and second jaw members includes a plurality of ring-like electrodes disposed thereon having a first electrical potential and at least one of the first and second jaw members includes a corresponding plurality of post electrodes disposed thereon having a second electrical potential. Each of the plurality of post electrodes is concentrically and inwardly disposed of a respective ring electrode to form an electrode micro-sealing pad. Upon activation of the forceps, tissue grasped between the each of the plurality of electrode micro-sealing pads of the jaw members is sealed while tissue adjacent to each of the electrode micro-sealing pads remains viable.

In one embodiment, the ring electrode are disposed on one of the first and second jaw members and the post electrodes are dispose on the other of the first and second jaw members. Alternatively, the ring electrodes and the post electrodes are dispose on the same jaw member. An electrically insulative material is disposed between each ring electrode and the corresponding post electrode of each electrode micro-sealing pad. Preferably, the electrode micro-sealing pads are arranged in a pattern-like manner across and/or along the jaw members.

In another embodiment, the forceps includes a ratchet or handle mechanism which provides a closure pressure in the range of about 3 kg/cm$^2$ to about 16 kg/cm$^2$ between opposing jaw members distributed over tissue contact surfaces. At least one non-conductive stop member may be disposed on one or both jaw members to control the distance between opposing jaw members when tissue is held therebetween. Preferably, at least one of the jaw members includes a non-stick coating disposed on the tissue engaging surfaces of each electrode micro-sealing pad and/or other tissue engaging surfaces of the jaw members. Preferably, the non-stick coating includes one or a combination of one or more of the following materials: TiN, ZrN, TiAlN, CrN, nickel/chrome alloys with a Ni/Cr ratio of approximately 5:1, Inconel 600, Ni200 and Ni201.

In yet another embodiment, each of the electrodes micro-sealing pads is separated by a distance in the range of about 0.020 inches to about 0.2 inches from any adjacent pad. The electrode micro-sealing pads may be flush with the non-conductive tissue engaging surfaces of the jaw members and a series of stop members regulate the distance between opposing jaw members. Alternatively, the electrode micro-sealing pads may protrude from about 0.001 inches to about 0.2 inches from one of the first and second jaw members and regulate the distance between the jaw members for effective micro-sealing.

BRIEF DESCRIPTION OF THE DRAWINGS

Various embodiments of the subject instrument are described herein with reference to the drawings wherein:

FIG. 3A is an enlarged, schematic view of one embodiment of the electrode assembly showing a pair of opposing, concentrically-oriented electrodes disposed on a pair of opposing jaw members;

FIG. 3B is a partial, side cross-sectional view of the electrode assembly of FIG. 3A;

DETAILED DESCRIPTION

Figure 1A:
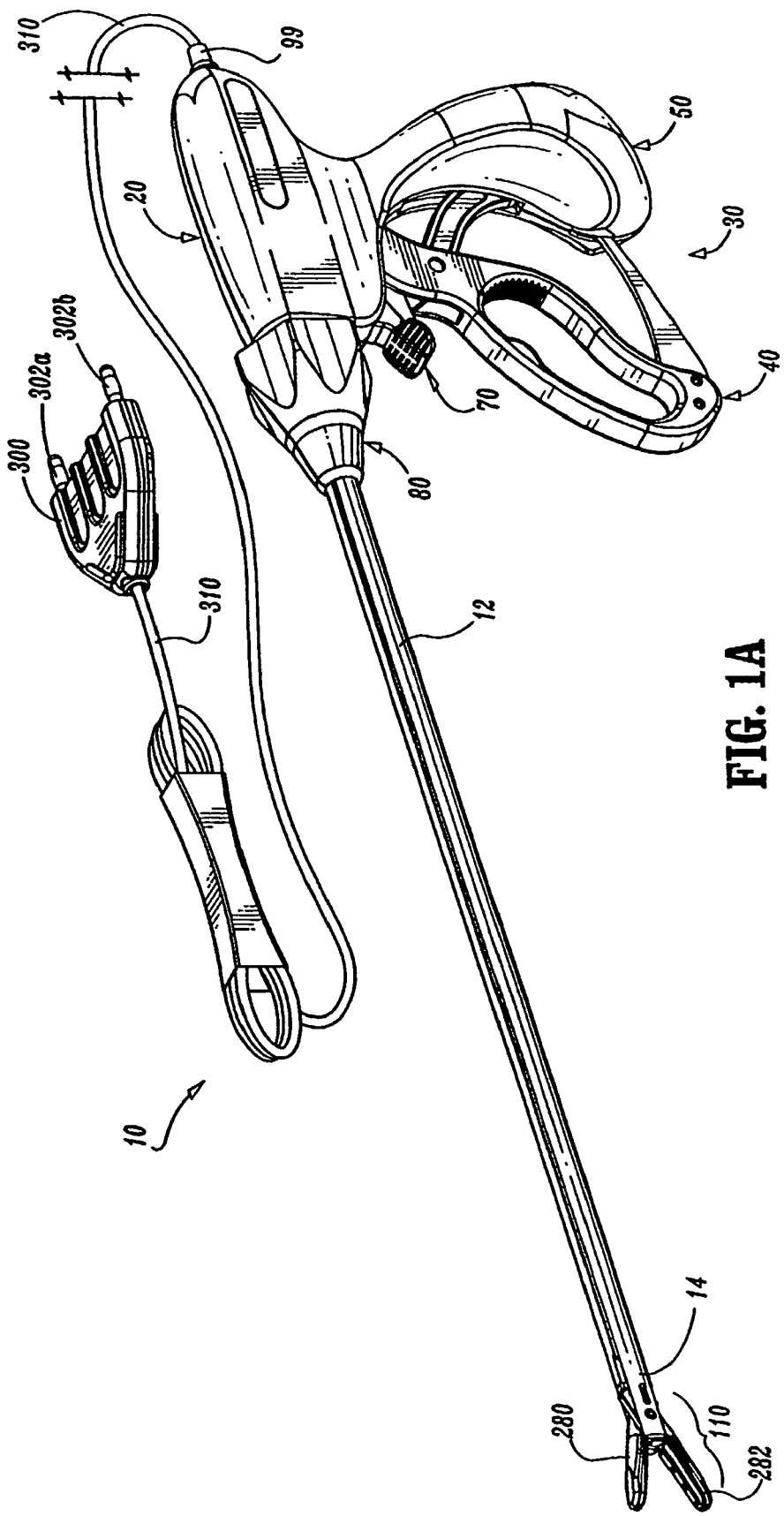
FIG. 1A is a perspective view of an endoscopic forceps having an electrode assembly in accordance with the present disclosure.

Referring now to FIG. 1A, a bipolar forceps 10 is shown for use with various surgical procedures. Forceps 10 generally includes a housing 20, a handle assembly 30, a rotating assembly 80, an activation assembly 70 and an electrode assembly 110 which mutually cooperate to grasp and seal tissue 600 (See FIGS. 5A-5C). Although the majority of the figure drawings depict a bipolar forceps 10 for use in connection with endoscopic surgical procedures, an open forceps 200 is also contemplated for use in connection with traditional open surgical procedures and is shown by way of example in FIG. 1B and is described below. For the purposes herein, either an endoscopic instrument or an open instrument may be utilized with the electrode assembly described herein. Obviously, different electrical and mechanical connections and considerations apply to each particular type of instrument, however, the novel aspects with respect to the electrode assembly and its operating characteristics remain generally consistent with respect to both the open or endoscopic designs.

More particularly, forceps 10 includes a shaft 12 which has a distal end 14 dimensioned to mechanically engage a jaw assembly 110 and a proximal end 16 which mechanically engages the housing 20. The shaft 12 may be bifurcated at the distal end 14 thereof to receive the jaw assembly 110. The proximal end 16 of shaft 12 mechanically engages the rotating assembly 80 to facilitate rotation of the jaw assembly 110. In the drawings and in the descriptions which follow, the term "proximal", as is traditional, will refer to the end of the forceps 10 which is closer to the user, while the term "distal" will refer to the end which is further from the user.

Forceps 10 also includes an electrical interface or plug 300 which connects the forceps 10 to a source of electrosurgical energy, e.g., an electrosurgical generator 350 (See FIG. 3B). Plug 300 includes a pair of prong members 302a and 302b which are dimensioned to mechanically and electrically connect the forceps 10 to the electrosurgical generator 350. An electrical cable 310 extends from the plug 300 to a sleeve 99 which securely connects the cable 310 to the forceps 10. Cable 310 is internally divided within the housing 20 to transmit electrosurgical energy through various electrical feed paths to the jaw assembly 110 as explained in more detail below.

Handle assembly 30 includes a fixed handle 50 and a movable handle 40. Fixed handle 50 is integrally associated with housing 20 and handle 40 is movable relative to fixed handle 50 to actuate a pair of opposing jaw members 280 and 282 of the jaw assembly 110 as explained in more detail below. The activation assembly 70 is selectively movable by the surgeon to energize the jaw assembly 110. Movable handle 40 and activation assembly 70 are preferably of unitary construction and are operatively connected to the housing 20 and the fixed handle 50 during the assembly process.

As mentioned above, jaw assembly 110 is attached to the distal end 14 of shaft 12 and includes a pair of opposing jaw members 280 and 282. Movable handle 40 of handle assembly 30 imparts movement of the jaw members 280 and 282 from an open position wherein the jaw members 280 and 282 are disposed in spaced relation relative to one another for approximating tissue 600, to a clamping or closed position wherein the jaw members 280 and 282 cooperate to grasp tissue 600 therebetween (See FIGS. 5A-5C).

It is envisioned that the forceps 10 may be designed such that it is fully or partially disposable depending upon a particular purpose or to achieve a particular result. For example, jaw assembly 110 may be selectively and releasably engageable with the distal end 14 of the shaft 12 and/or the proximal end 16 of shaft 12 may be selectively and releasably engageable with the housing 20 and the handle assembly 30. In either of these two instances, the forceps 10 would be considered "partially disposable" or "reposable", i.e., a new or different jaw assembly 110 (or jaw assembly 110 and shaft 12) selectively replaces the old jaw assembly 110 as needed.

Figure 1B:
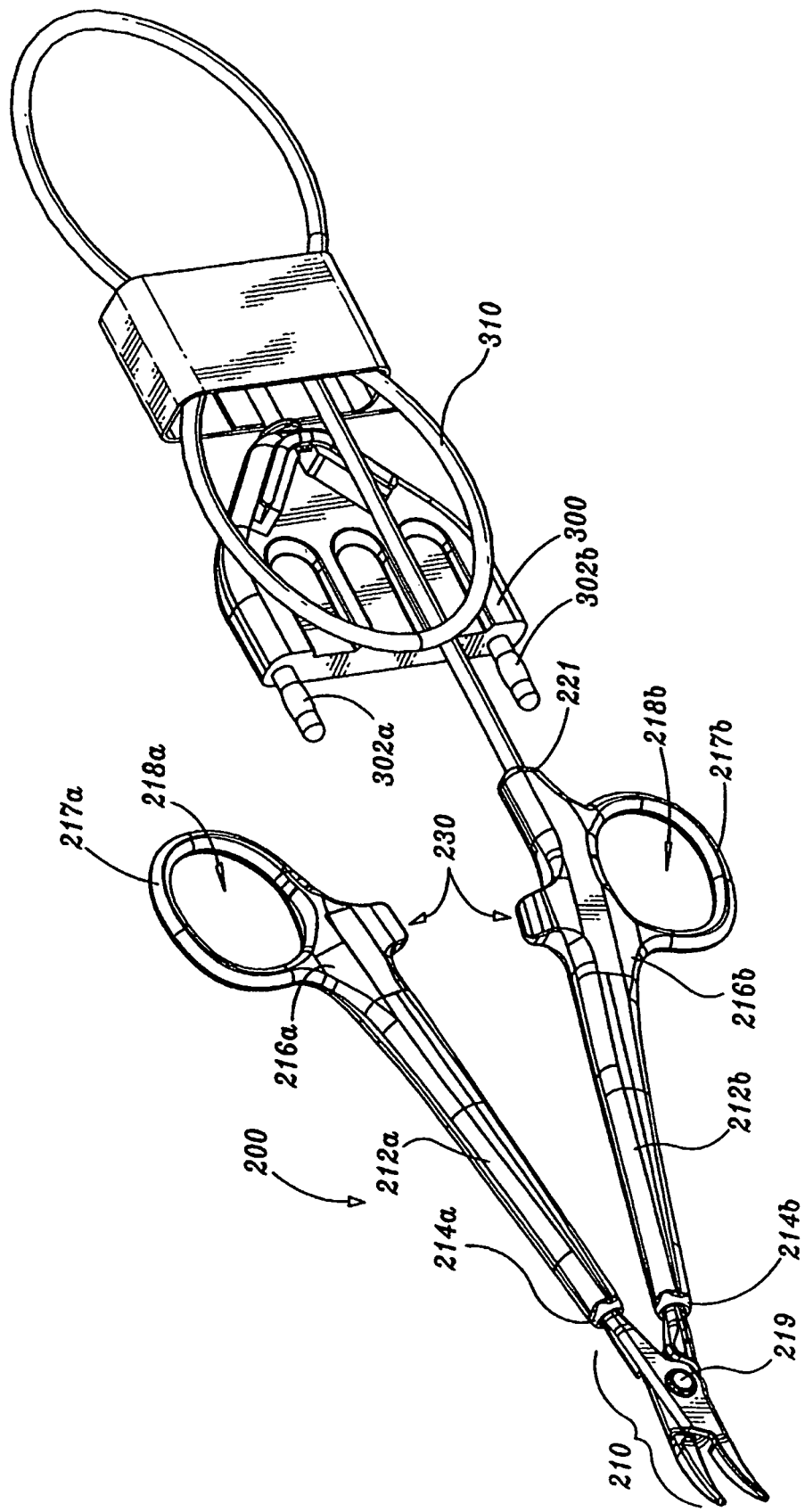
FIG. 1B is a perspective view of an open forceps having a electrode assembly in accordance with the present disclosure.
Figure 2:
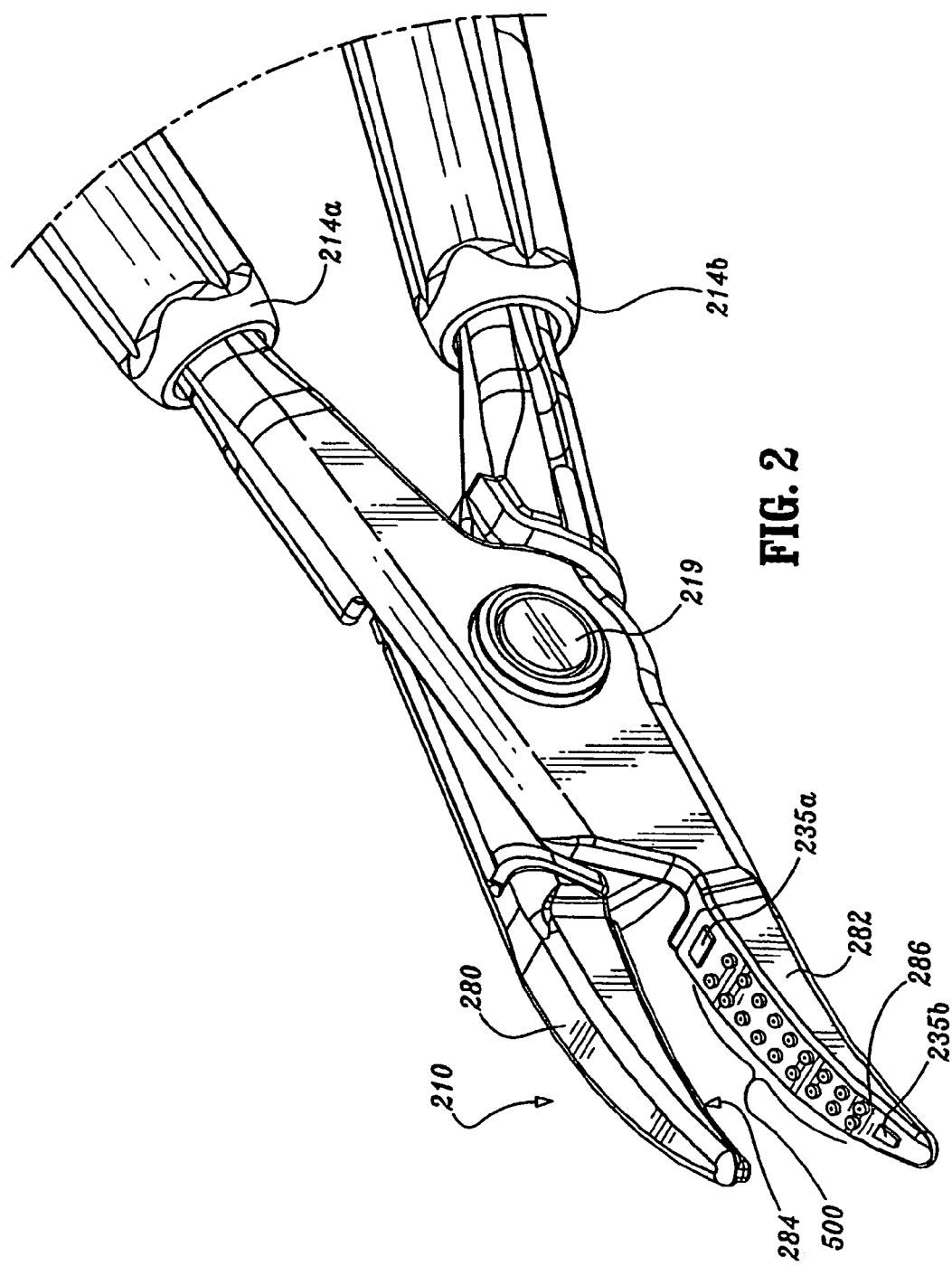
FIG. 2 is an enlarged, perspective view of the electrode assembly of the forceps of FIG. 1B shown in an open configuration.

Referring now to FIGS. 1B and 2, an open forceps 200 includes a pair of elongated shaft portions 212a each having a proximal end 216a and 216b, respectively, and a distal end 214a and 214b, respectively. The forceps 200 includes jaw assembly 210 which attaches to distal ends 214a and 214b of shafts 212a and 212b, respectively. Jaw assembly 210 includes opposing jaw members 280 and 282 which are pivotably connected about a pivot pin 219.

Preferably, each shaft 212a and 212b includes a handle 217a and 217b disposed at the proximal end 216a and 216b thereof which each define a finger hole 218a and 218b, respectively, therethrough for receiving a finger of the user. As can be appreciated, finger holes 218a and 218b facilitate movement of the shafts 212a and 212b relative to one another which, in turn, pivot the jaw members 280 and 282 from an open position wherein the jaw members 280 and 282 are disposed in spaced relation relative to one another for approximating tissue 600 to a clamping or closed position wherein the jaw members 280 and 282 cooperate to grasp tissue 600 therebetween. A ratchet 230 is preferably included for selectively locking the jaw members 280 and 282 relative to one another at various positions during pivoting.

Preferably, each position associated with the cooperating ratchet interfaces 230 holds a specific, i.e., constant, strain energy in the shaft members 212a and 212b which, in turn, transmits a specific closing force to the jaw members 280 and 282. It is envisioned that the ratchet 230 may include graduations or other visual markings which enable the user to easily and quickly ascertain and control the amount of closure force desired between the jaw members 280 and 282.

One of the shafts, e.g., 212b, includes a proximal shaft connector/flange 221 which is designed to connect the forceps 200 to a source of electrosurgical energy such as an electrosurgical generator 350 (FIG. 3B). More particularly, flange 221 mechanically secures electrosurgical cable 310 to the forceps 200 such that the user may selectively apply electrosurgical energy as needed. The proximal end of the cable 310 includes a similar plug 300 as described above with respect to FIG. 1A. The interior of cable 310 houses a pair of leads which conduct different electrical potentials from the electrosurgical generator 350 to the jaw members 280 and 282 as explained below with respect to FIG. 2.

Preferably, the jaw members 280 and 282 are generally symmetrical and include similar component features which cooperate to permit facile rotation about pivot 219 to effect the grasping of tissue 600. Each jaw member 280 and 282 includes a non-conductive tissue contacting surface 284 and 286, respectively, which cooperate to engage the tissue 600 during treatment.

As best shown in FIG. 2, the various electrical connections of the electrode assembly 210 are preferably configured to provide electrical continuity to an array of electrode micro-sealing pads 500 of disposed across one or both jaw members 280 and 282. The electrical paths 416, 426 or 516, 526 from the array of electrode micro-sealing pads 500 are preferably mechanically and electrically interfaced with corresponding electrical connections (not shown) disposed within shafts 212a and 212b, respectively. As can be appreciated, these electrical paths 416, 426 or 516, 526 may be permanently soldered to the shafts 212a and 212b during the assembly process of a disposable instrument or, alternatively, selectively removable for use with a reposable instrument.

Figure 4A:
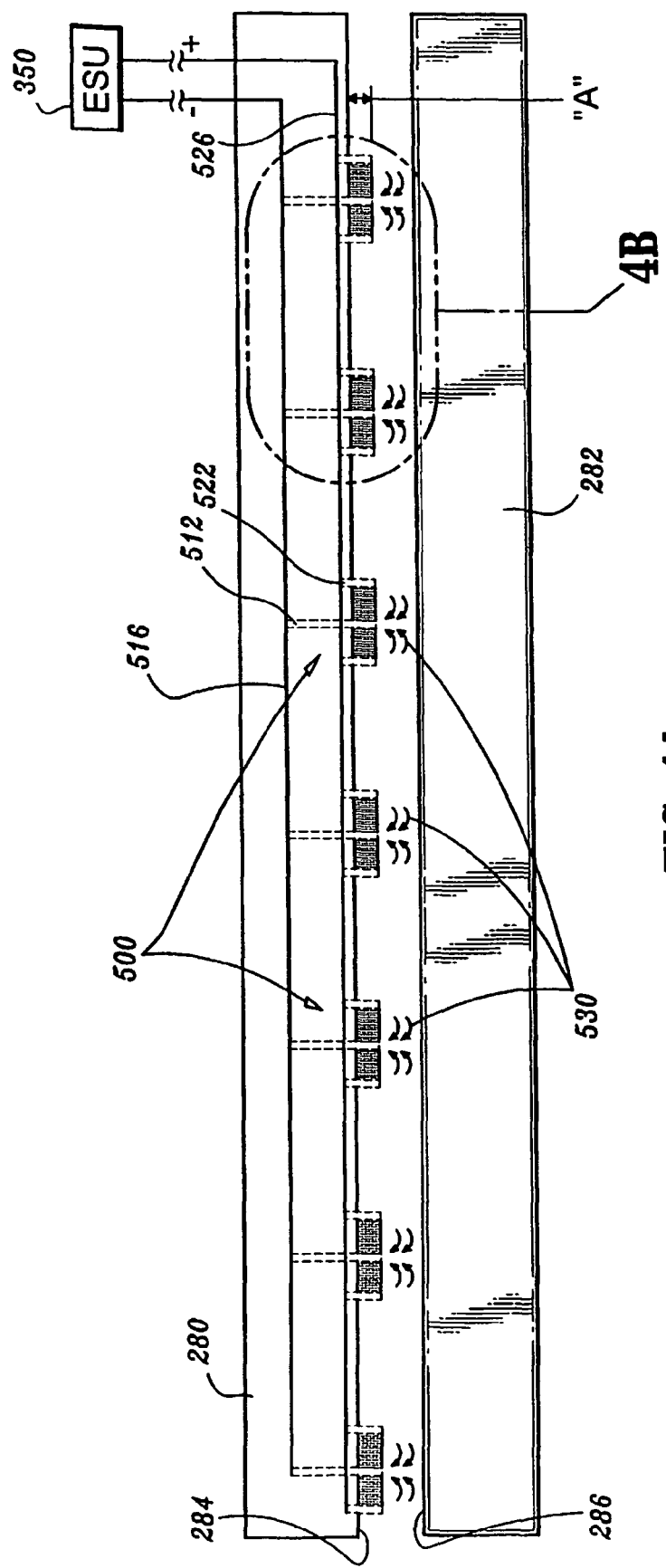
FIG. 4A is an enlarged, schematic view of another embodiment of the electrode assembly showing a plurality of concentrically-oriented electrode micro-sealing pads disposed on the same jaw member.
Figure 4B:
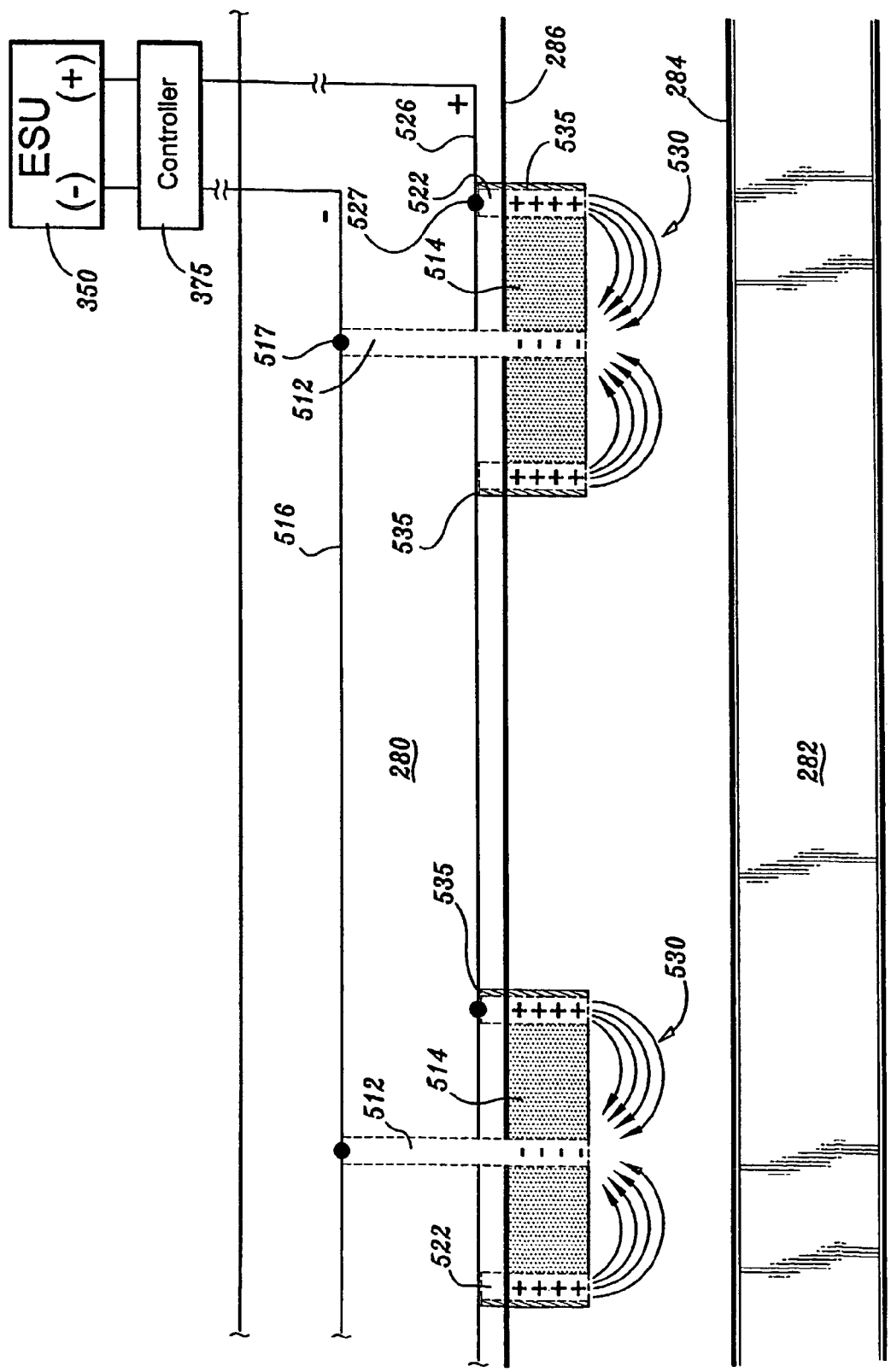
FIG. 4B is a greatly enlarged view of the area of detail in FIG. 4A showing the electrical path during activation of the electrode assembly.
Figure 4C:
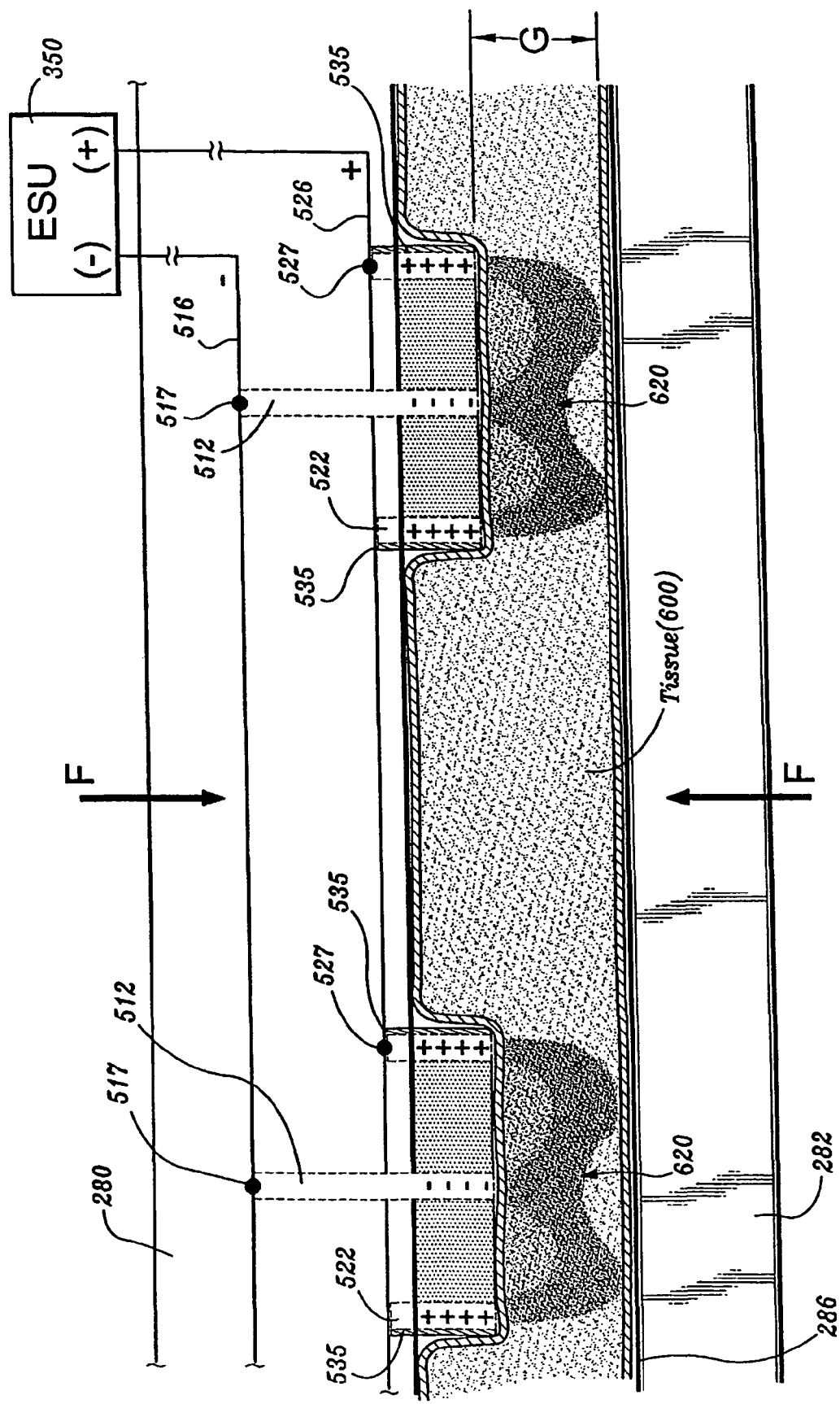
FIG. 4C is an enlarged schematic view showing the individual micro-sealing sites and viable tissue areas between the two jaw members after activation.

As best shown in FIGS. 4A-4C, the electrical paths are connected to the plurality of electrode micro-sealing pads 500 within the jaw assembly 210. More particularly, the first electrical path 526 (i.e., an electrical path having a first electrical potential) is connected to each ring electrode 522 of each electrode micro-sealing pad 500. The second electrical path 516 (i.e., an electrical path having a second electrical potential) is connected to each post electrode 522 of each electrode micro-sealing pad 500.

Preferably, the electrical paths 516 and 526 do not encumber the movement of the jaw members 280 and 282 relative to one another during the manipulation and grasping of tissue 400. Likewise, the movement of the jaw members 280 and 282 do not unnecessarily strain the electrical paths 516 and 526 or their respective connections 517, 527.

As best seen in FIGS. 2-5C, jaw members 280 and 282 both include non-conductive tissue contacting surfaces 284 and 286, respectively, disposed along substantially the entire longitudinal length thereof (i.e., extending substantially from the proximal to distal end of each respective jaw member 280 and 284). Preferably, the non-conductive tissue contacting surfaces 284 and 286 are made from an insulative material such as ceramic due to its hardness and inherent ability to withstand high temperature fluctuations. Alternatively, the non-conductive tissue contacting surfaces 284 and 286 may be made from a material or a combination of materials having a high Comparative Tracking Index (CTI) in the range of about 300 to about 600 volts. Examples of high CTI materials include nylons and syndiotactic polystryrenes such as QUESTRA® manufactured by DOW Chemical. Other materials may also be utilized either alone or in combination, e.g., Nylons, Syndiotactic-polystryrene (SPS), Polybutylene Terephthalate (PBT), Polycarbonate (PC), Acrylonitrile Butadiene Styrene (ABS), Polyphthalamide (PPA), Polymide, Polyethylene Terephthalate (PET), Polyamide-imide (PAI), Acrylic (PMMA), Polystyrene (PS and HIPS), Polyether Sulfone (PES), Aliphatic Polyketone, Acetal (POM) Copolymer, Polyurethane (PU and TPU), Nylon with Polyphenylene-oxide dispersion and Acrylonitrile Styrene Acrylate. Preferably, the non-conductive tissue contacting surfaces 284 and 286 are dimensioned to securingly engage and grasp the tissue 600 and may include serrations (not shown) or roughened surfaces to facilitate approximating and grasping tissue.

It is envisioned that one of the jaw members, e.g., 282, includes at least one stop member 235a, 235b (FIG. 2) disposed on the inner facing surface of the sealing surfaces 286. Alternatively or in addition, one or more stop members 235a, 235b may be positioned adjacent to the non-conductive sealing surfaces 284, 286 or proximate the pivot 219. The stop members 235a, 235b are preferably designed to define a gap "G" (FIG. 5B) between opposing jaw members 280 and 282 during the micro-sealing process. Preferably the separation distance during micro-sealing or the gap distance "G" is within the range of about 0.001 inches (~0.03 millimeters) to about 0.006 inches (~0.016 millimeters). One or more stop members 235a, 235b may be positioned on the distal end and proximal end of one or both of the jaw members 280, 282 or may be positioned between adjacent electrode micro-sealing pads 500. Moreover, the stop members 235a and 235b may be integrally associated with the non-conductive tissue contacting surfaces 284 and 286. It is envisioned that the array of electrode micro-sealing pads 500 may also act as stop members for regulating the distance "G" between opposing jaw members 280, 282 (See FIG. 4C).

As mentioned above, the effectiveness of the resulting micro-seal is dependent upon the pressure applied between opposing jaw members 280 and 282, the pressure applied by each electrode micro-sealing pad 500 at each micro-sealing site 620 (FIG. 4C), the gap "G" between the opposing jaw members 280 and 282 (either regaled by a stop member 235a, 235b or the array of electrode micro-sealing pads 500) and the control of the electrosurgical intensity during the micro-sealing process. Applying the correct force is important to oppose the walls of the tissue; to reduce the tissue impedance to a low enough value that allows enough current through the tissue; and to overcome the forces of expansion during tissue heating in addition to contributing towards creating the required end tissue thickness which is an indication of a good micro-seal. Regulating the gap distance and regulating the electrosurgical intensity ensure a consistent seal quality and reduce the likelihood of collateral damage to surrounding tissue.

As best show in FIG. 2, the electrode micro-sealing pads 500 are arranged in a longitudinal, pair-like fashion along the tissue contacting surfaces 286 and/or 284. Preferably, two or more micro-sealing pads 500 may extend transversally across the tissue contacting surface 286. FIGS. 3A and 3B show one embodiment of the present disclosure wherein the electrode micro-sealing pads 500 include a ring electrode 422 disposed on one jaw members 282 and a post electrode 412 disposed on the other jaw member 280. The ring electrode 422 includes an insulating material 424 disposed therein to form a ring electrode and insulator assembly 420 and the post electrode 422 includes an insulating material disposed therearound to form a post electrode and insulator assembly 430. Each post electrode assembly 430 and the ring electrode assembly 420 of this embodiment together define one electrode micro-sealing pad 400. Although shown as a circular-shape, ring electrode 422 may assume any other annular or enclosed configuration or alternatively partially enclosed configuration such as a C-shape arrangement.

As best shown in FIG. 3B, the post electrode 422 is concentrically centered opposite the ring electrode 422 such that when the jaw members 280 and 282 are closed about the tissue 600, electrosurgical energy flows from the ring electrode 422, through tissue 600 and to the post electrode 412. The insulating materials 414 and 424 isolate the electrodes 412 and 422 and prevent stray current tracking to surrounding tissue. Alternatively, the electrosurgical energy may flow from the post electrode 412 to the ring electrode 422 depending upon a particular purpose.

FIGS. 4A-4C show an alternate embodiment of the jaw assembly 210 according to the present disclosure for micro-sealing tissue 600 wherein each electrode micro-sealing pad 500 is disposed on a single jaw member, e.g., jaw member 280. More particularly and as best illustrated in FIG. 4B, each electrode micro-sealing pad 500 consists of an inner post electrode 512 which is surrounded by an insulative material 514, e.g., ceramic. The insulative material 514 is, in turn, encapsulated by a ring electrode 522. Preferably, a second insulative material 535 (or the same insulative material 514) encases the ring electrode 522 to prevent stray electrical currents to surrounding tissue.

The ring electrode 522 is connected to the electrosurgical generator 350 by way of a cable 526 (or other conductive path) which transmits a first electrical potential to each ring electrode 522 at connection 527. The post electrode 512 is connected to the electrosurgical generator 350 by way of a cable 516 (or other conductive path) which transmits a second electrical potential to each post electrode 522 at connection 517. A controller 375 (See FIG. 4B) may be electrically interposed between the generator 350 and the electrodes 512, 522 to regulate the electrosurgical energy supplied thereto depending upon certain electrical parameters, current impedance, temperature, voltage, etc. For example, the instrument or the controller may include one or more smart sensors (not shown) which communicate with the electrosurgical generator 350 (or smart circuit, computer, feedback loop, etc.) to automatically regulate the electrosurgical intensity (waveform, current, voltage, etc.) to enhance the micro-sealing process. The sensor may measure or monitor one or more of the following parameters: tissue temperature, tissue impedance at the micro-seal, change in impedance of the tissue over time and/or changes in the power or current applied to the tissue over time. An audible or visual feedback monitor (not shown) may be employed to convey information to the surgeon regarding the overall micro-seal quality or the completion of an effective tissue micro-seal.

Moreover, a PCB circuit of flex circuit (not shown) may be utilized to provide information relating to the gap distance (e.g., a proximity detector may be employed) between the two jaw members 280 and 282, the micro-sealing pressure between the jaw members 280 and 282 prior to and during activation, load (e.g., strain gauge may be employed), the tissue thickness prior to or during activation, the impedance across the tissue during activation, the temperature during activation, the rate of tissue expansion during activation and micro-sealing. It is envisioned that the PCB circuit may be designed to provide electrical feedback to the generator 350 relating to one or more of the above parameters either on a continuous basis or upon inquiry from the generator 350. For example, a PCB circuit may be employed to control the power, current and/or type of current waveform from the generator 350 to the jaw members 280, 282 to reduce collateral damage to surrounding tissue during activation, e.g., thermal spread, tissue vaporization and/or steam from the treatment site. Examples of a various control circuits, generators and algorithms which may be utilized are disclosed in U.S. Pat. No. 6,228,080 and U.S. application Ser. No. 10/073,761 the entire contents of both of which are hereby incorporated by reference herein.

Figure 5A:
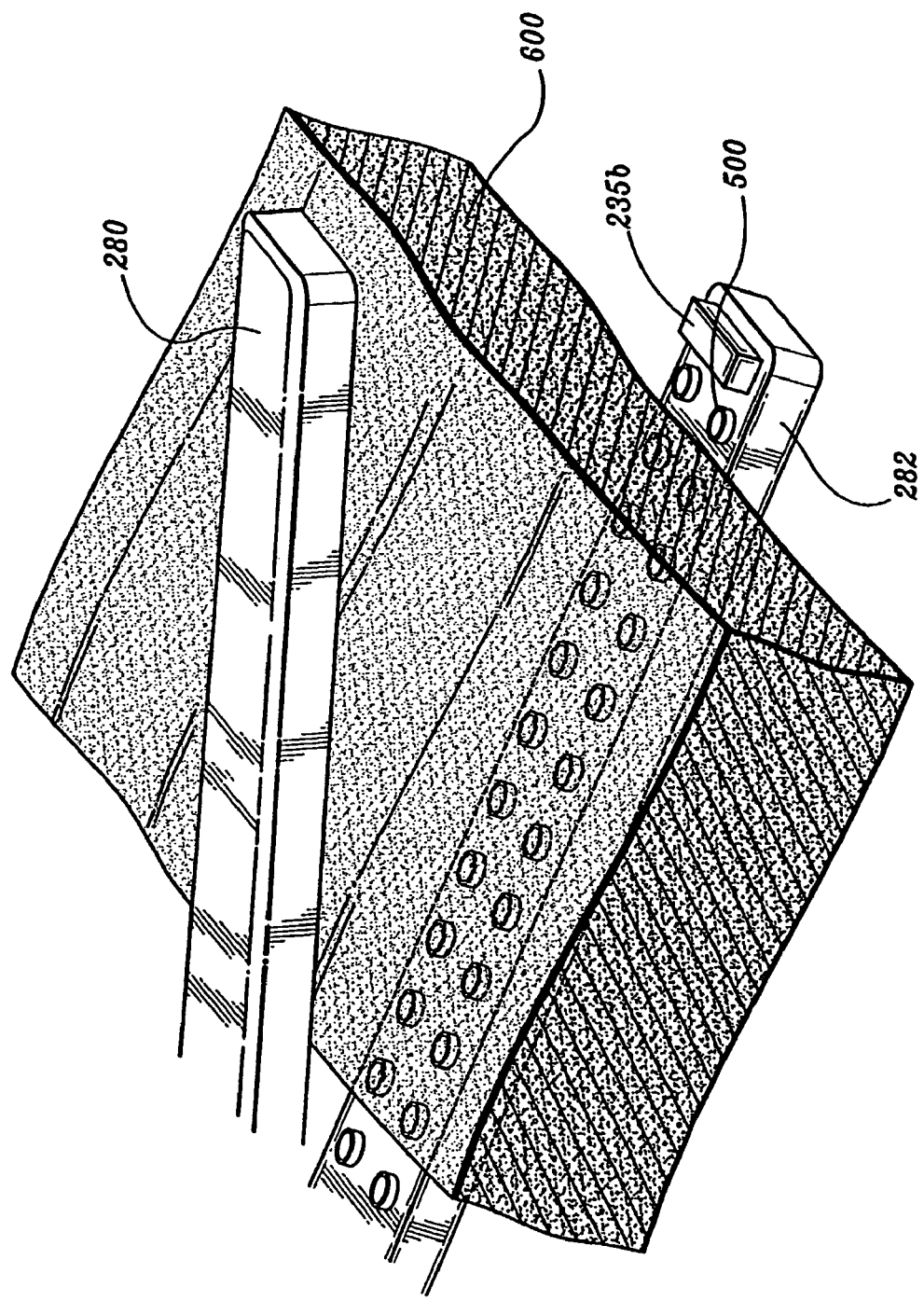
FIG. 5A is a schematic, perspective view of the jaw members approximating tissue.
Figure 5B:
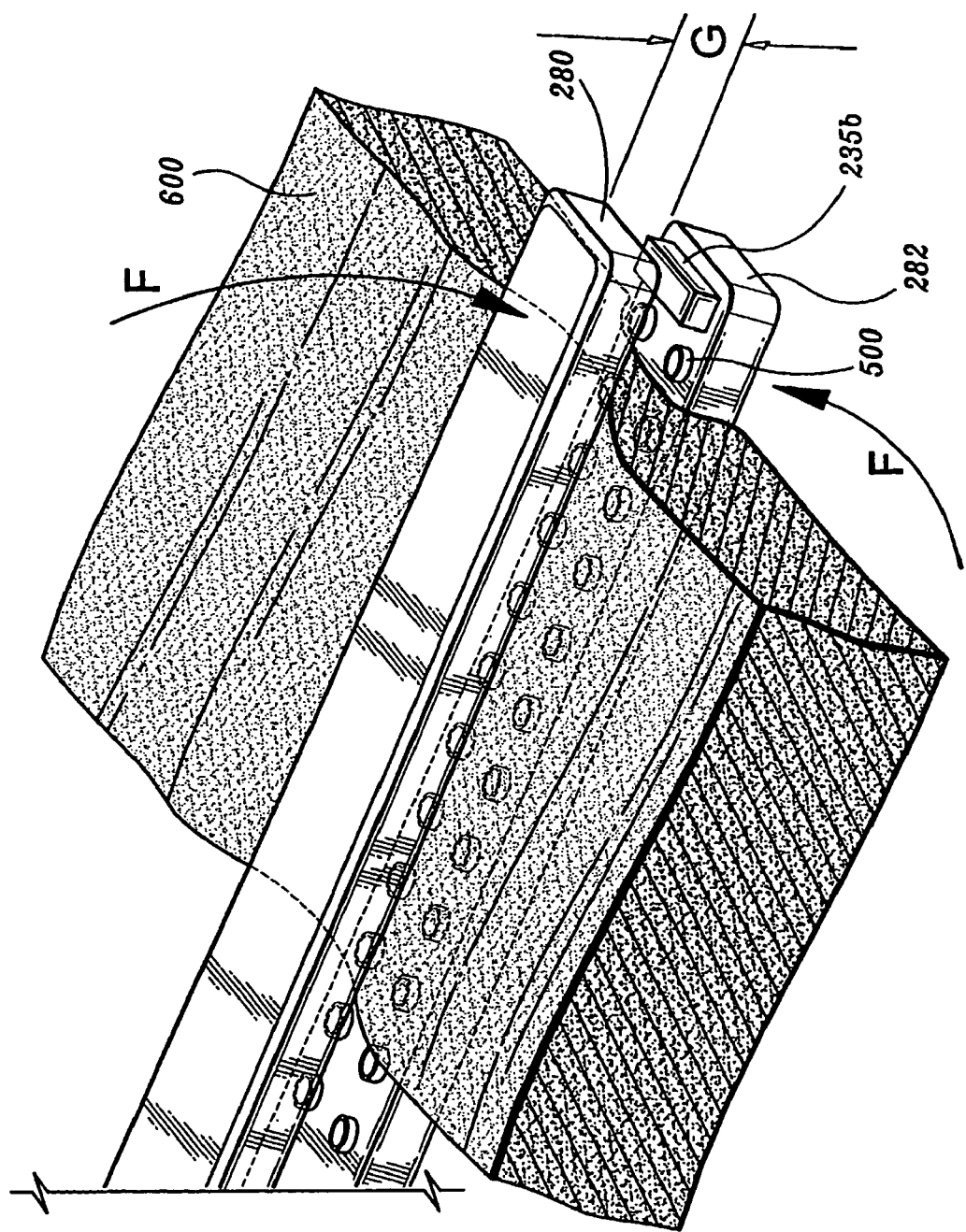
FIG. 5B is a schematic, perspective view of the jaw members grasping tissue.
Figure 5C:
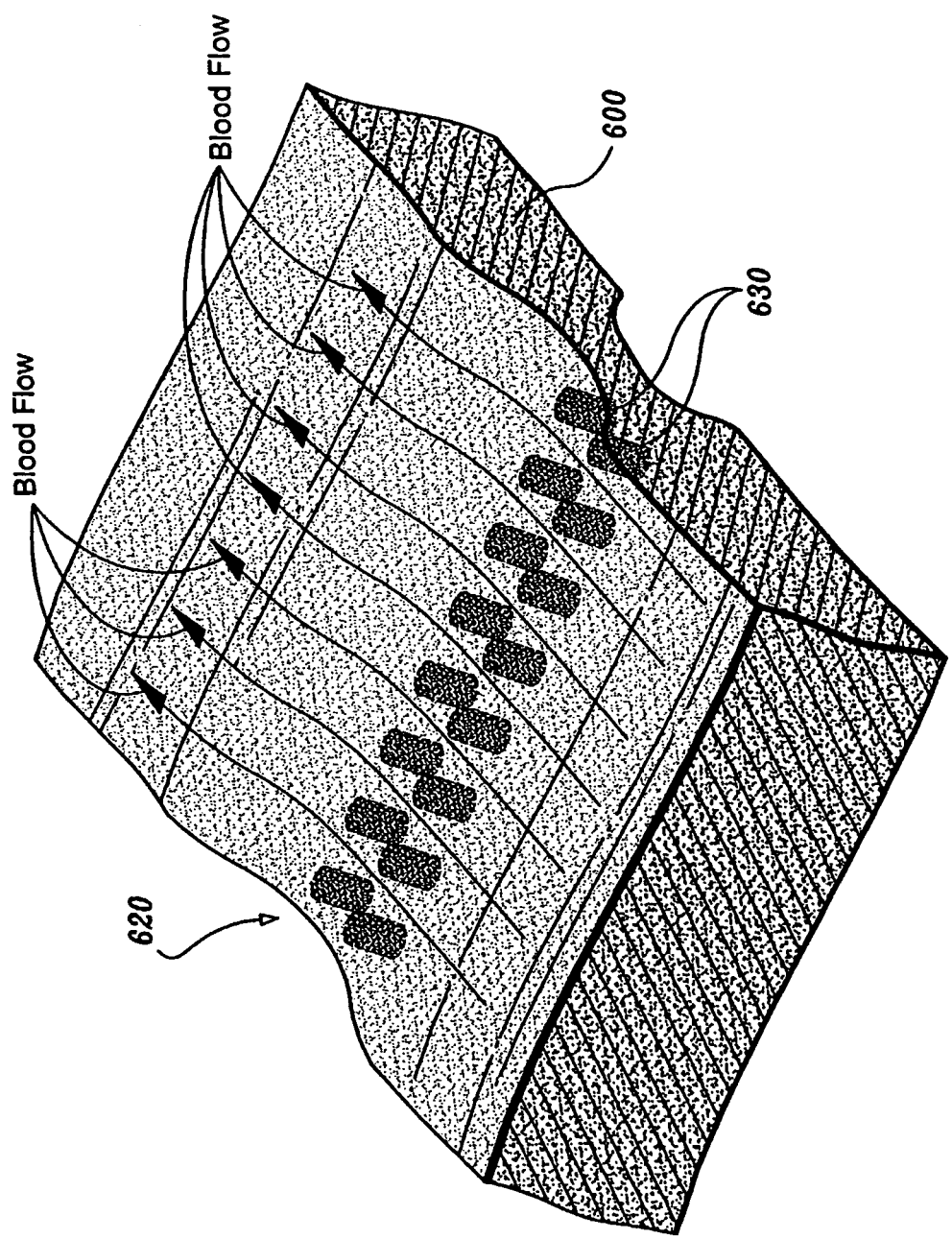
FIG. 5C is a schematic, perspective view showing a series of micro-seals disposed in a pattern across the tissue after activation of the electrode assembly.

In use as depicted in FIGS. 5A-5C, the surgeon initially approximates the tissue (FIG. 5A) between the opposing jaw member 280 and 282 and then grasps the tissue 600 (FIG. 5B) by actuating the jaw members 280, 282 to rotate about pivot 219. Once the tissue is grasped, the surgeon selectively activates the generator 350 to supply electrosurgical energy to the array of the electrode micro-sealing pads 500. More particularly, electrosurgical energy flows from the ring electrode 522, through the tissue 600 and to the post electrode 512 (See FIGS. 4B and 4C). As a result thereof, an intermittent pattern of individual micro-seals 630 is created along and across the tissue 600 (See FIG. 5C). The arrangement of the micro-sealing pads 500 across the tissue only seals the tissue which is between each micro-sealing pad 500 and the opposing jaw member 282. The adjacent tissue remains viable which, as can be appreciated, allows blood and nutrients to flow through the sealing site 620 and between the individual micro-seals 630 to promote tissue healing and reduce the chances of tissue necrosis. By selectively regulating the closure pressure "F", gap distance "G", and electrosurgical intensity, effective and consistent micro-seals 630 may be created for many different tissue types.

It is further envisioned that selective ring electrodes and post electrodes may have varying electric potentials upon activation. For example, at or proximate the distal tip of one of the jaw members, one or a series of electrodes may be electrically connected to a first potential and the corresponding electrodes (either on the same jaw or perhaps the opposing jaw) may be connected to a second potential. Towards the proximal end of the jaw member, one or a series of electrodes may be connected to a third potential and the corresponding electrodes connected to yet a fourth potential. As can be appreciated, this would allow different types of tissue sealing to take place at different portions of the jaw members upon activation. For example, the type of sealing could be based upon the type of tissues involved or perhaps the thickness of the tissue. To seal larger tissue, the user would grasp the tissue more towards the proximal portion of the opposing jaw members and to seal smaller tissue, the user would grasp the tissue more towards the distal portion of the jaw members. It is also envisioned that the pattern and/or density of the micro-sealing pads may be configured to seal different types of tissue or thicknesses of tissue along the same jaw members depending upon where the tissue is grasped between opposing jaw members.

From the foregoing and with reference to the various figure drawings, those skilled in the art will appreciate that certain modifications can also be made to the present disclosure without departing from the scope of the same. For example, it is envisioned that by making the forceps 100, 200 disposable, the forceps 100, 200 is less likely to become damaged since it is only intended for a single use and, therefore, does not require cleaning or sterilization. As a result, the functionality and consistency of the vital micro-sealing components, e.g., the conductive micro-sealing electrode pads 500, the stop member(s) 235a, 235b, and the insulative materials 514, 535 will assure a uniform and quality seal.

Experimental results suggest that the magnitude of pressure exerted on the tissue by the micro-sealing pads 112 and 122 is important in assuring a proper surgical outcome, maintaining tissue viability. Tissue pressures within a working range of about 3 kg/cm$^2$ to about 16 kg/cm$^2$ and, preferably, within a working range of 7 kg/cm$^2$ to 13 kg/cm$^2$ have been shown to be effective for micro-sealing various tissue types and vascular bundles.

In one embodiment, the shafts 212a and 212b are manufactured such that the spring constant of the shafts 212a and 212b, in conjunction with the placement of the interfacing surfaces of the ratchet 230, will yield pressures within the above working range. In addition, the successive positions of the ratchet interfaces increase the pressure between opposing micro-sealing surfaces incrementally within the above working range.

It is envisioned that the outer surface of the jaw members 280 and 282 may include a nickel-based material or coating which is designed to reduce adhesion between the jaw members 280, 282 (or components thereof) with the surrounding tissue during activation and micro-sealing. Moreover, it is also contemplated that other components such as the shaft portions 212a, 212b and the rings 217a, 217b may also be coated with the same or a different "non-stick" material. Preferably, the non-stick materials are of a class of materials that provide a smooth surface to prevent mechanical tooth adhesions.

It is also contemplated that the tissue contacting portions of the electrodes and other portions of the micro-sealing pads 400, 500 may also be made from or coated with non-stick materials. When utilized on these tissue contacting surfaces, the non-stick materials provide an optimal surface energy for eliminating sticking due in part to surface texture and susceptibility to surface breakdown due electrical effects and corrosion in the presence of biologic tissues. It is envisioned that these materials exhibit superior non-stick qualities over stainless steel and should be utilized in areas where the exposure to pressure and electrosurgical energy can create localized "hot spots" more susceptible to tissue adhesion. As can be appreciated, reducing the amount that the tissue "sticks" during micro-sealing improves the overall efficacy of the instrument.

The non-stick materials may be manufactured from one (or a combination of one or more) of the following "non-stick" materials: nickel-chrome, chromium nitride, MedCoat 2000 manufactured by The Electrolizing Corporation of OHIO, Inconel 600 and tin-nickel. Inconel 600 coating is a so-called "super alloy" which is manufactured by Special Metals, Inc. located in Conroe Tex. The alloy is primarily used in environments which require resistance to corrosion and heat. The high Nickel content of Inconel 600 makes the material especially resistant to organic corrosion. As can be appreciated, these properties are desirable for bipolar electrosurgical instruments which are naturally exposed to high temperatures, high RF energy and organic matter. Moreover, the resistivity of Inconel 600 is typically higher than the base electrode material which further enhances desiccation and micro-seal quality.

One particular class of materials disclosed herein has demonstrated superior non-stick properties and, in some instances, superior micro-seal quality. For example, nitride coatings which include, but are not not limited to: TiN, ZrN, TiAlN, and CrN are preferred materials used for non-stick purposes. CrN has been found to be particularly useful for non-stick purposes due to its overall surface properties and optimal performance. Other classes of materials have also been found to reducing overall sticking. For example, high nickel/chrome alloys with a Ni/Cr ratio of approximately 5:1 have been found to significantly reduce sticking in bipolar instrumentation.

It is also envisioned that the micro-sealing pads 400, 500 may be arranged in many different configurations across or along the jaw members 280, 282 depending upon a particular purpose. Moreover, it is also contemplated that a knife or cutting element (not shown) may be employed to sever the tissue 600 between a series of micro-sealing pads 400, 500 depending upon a particular purpose. The cutting element may include a cutting edge to simply mechanically cut tissue 600 and/or may be configured to electrosurgically cut tissue 600.

While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of preferred embodiments. Those skilled in the art will envision other modifications within the scope and spirit of the claims appended hereto.

What is claimed is:

1. A bipolar electrosurgical forceps, comprising:
   first and second opposing jaw members having respective tissue engaging surfaces associated therewith, said first and second jaw members adapted for relative movement between an open position to receive tissue and a closed position engaging tissue between said tissue engaging surfaces; and
   at least one of said first and second jaw members including a substantially annular electrode mounted to said tissue engaging surface thereof, at least one of said first and second jaw members including a corresponding post electrode mounted to said tissue engaging surface thereof, said post electrode being in an inwardly disposed relation to said annular electrode when said jaw members are in at least said closed position to thereby define a micro-sealing pad whereby, upon energization, electrosurgical energy communicates between said post electrode and said annular electrode of said micro-sealing pad to thermally treat tissue disposed therebetween.

2. A bipolar electrosurgical forceps according to claim 1 including a plurality of annular electrodes and a plurality of corresponding post electrodes arranged to define a plurality of micro-sealing pads.

3. A bipolar electrosurgical forceps according to claim 2 wherein said micro-sealing pads are arranged in a predetermined pattern along said first and second jaw members.

4. A bipolar electrosurgical forceps according to claim 3 wherein said micro-sealing pads are arranged in predetermined spaced relation along said first and second jaw members whereby upon energization tissue extending between adjacent micro-sealing pads remains substantially viable.

5. A bipolar electrosurgical forceps according to claim 4 wherein each micro-sealing pad is encapsulated by an electrically insulative material.

6. A bipolar electrosurgical forceps according to claim 1 wherein said annular electrode is disposed on said first jaw member and said post electrode is disposed on said second jaw member.

7. A bipolar electrosurgical forceps according to claim 1 wherein said annular electrode and said post electrode are disposed on said first jaw member.

8. A bipolar electrosurgical forceps according to claim 7 wherein an electrically insulative material is disposed between said ring electrode and said post electrode.

9. A bipolar electrosurgical forceps according to claim 1 further comprising means for providing a closure pressure in the range of about 3 kg/cm$^2$ to about 16 kg/cm$^2$ between opposing jaw members.

10. A bipolar electrosurgical forceps according to claim 1 wherein at least one of said first and second jaw members includes at least one non-conductive stop member disposed thereon to control the distance between said first and second jaw members when in said closed position thereof.

11. A bipolar electrosurgical forceps according to claim 4 wherein each of said electrode micro-sealing pads is separated from an adjacent electrode micro-sealing pad by a distance in the range of about 0.020 inches to about 0.2 inches.

12. A bipolar electrosurgical forceps according to claim 1 wherein at least one of said first and second jaw members includes a non-stick coating disposed on said tissue engaging surface of each electrode micro-sealing pad.

13. A bipolar electrosurgical forceps according to claim 12 wherein the non-stick coating includes one of: TiN, ZrN, TiAlN, CrN, nickel/chrome alloys with a Ni/Cr ratio of approximately 5:1, Inconel 600, Ni200 and Ni201.

14. A bipolar electrosurgical forceps according to claim 1 wherein said micro-sealing pad is dimensioned to protrude from one of said first and second jaw members to regulate the distance between said first and second jaw members when in said closed position.

15. A bipolar electrosurgical forceps according to claim 14 wherein said micro-sealing pad is dimensioned to protrude a distance "A" from one of said first and second jaw members, wherein the distance "A" is in the range of about 0.001 inches to about 0.2 inches.

16. A bipolar electrosurgical forceps, comprising:
first and second opposing jaw members each having a tissue engaging surface disposed thereon, said opposing jaw members being movable relative to one another from a first position to approximate tissue to a second position for engaging tissue therebetween;
at least one of said first and second jaw members including a plurality of ring electrodes disposed thereon having a first electrical potential and at least one of the first and second jaw members having a corresponding plurality of post electrodes disposed thereon having a second electrical potential wherein each of said plurality of post electrodes is inwardly disposed of a respective ring electrode to form an electrode micro-sealing pad;
such that upon activation of the forceps the amount of electrosurgical energy between each of said ring and post electrodes pairs is sufficient to seal tissue disposed therebetween while the amount of electrosurgical energy between adjacent electrode micro-sealing pads is substantially less such that the tissue disposed between adjacent electrode micro-sealing pads remains substantially viable after activation.

17. A bipolar electrosurgical forceps according to claim 16 wherein said ring electrode is disposed on one of said first and second jaw members and said post electrode is dispose on the other of said first and second jaw members.

18. A bipolar electrosurgical forceps according to claim 16 wherein said ring electrode and said post electrode are dispose on the same jaw member.

19. A bipolar electrosurgical forceps according to claim 18 wherein an electrically insulative material is disposed between the ring electrode and post electrode of each electrode micro-sealing pad.

20. A bipolar electrosurgical forceps according to claim 16 wherein said electrode micro-sealing pads are arranged in a pattern-like manner across said jaw members.

21. A bipolar electrosurgical forceps according to claim 16 further comprising means for providing a closure pressure in the range of about 3 kg/cm$^2$ to about 16 kg/cm$^2$ between opposing jaw members.

22. A bipolar electrosurgical forceps according to claim 16 wherein at least one of the jaw members includes at least one non-conductive stop member disposed thereon to control the distance between opposing jaw members when tissue is held therebetween.

23. A bipolar electrosurgical forceps according to claim 16 wherein each of said electrode micro-sealing pads is separated from an adjacent electrode micro-sealing pad by a distance in the range of about 0.020 inches to about 0.2 inches.

24. A bipolar electrosurgical forceps according to claim 16 wherein the electrode micro-sealing pads protrude from one of the first and second jaw members to regulate the distance between jaw members.

* * * * *